(12) United States Patent
Tsuchiya et al.

(10) Patent No.: US 8,105,799 B2
(45) Date of Patent: Jan. 31, 2012

(54) METHODS OF SCREENING COMPOUNDS INHIBITING SIGNAL TRANSDUCTION THROUGH INFLAMMATORY CYTOKINES

(75) Inventors: Masayuki Tsuchiya, Shizuoka (JP);
Toshihiko Ohtomo, Shizuoka (JP);
Yasuhiro Sugamata, Shizuoka (JP);
Kunihiro Matsumoto, Aichi (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 37 days.

(21) Appl. No.: 12/026,932

(22) Filed: Feb. 6, 2008

(65) Prior Publication Data

US 2008/0160541 A1    Jul. 3, 2008

Related U.S. Application Data

(63) Continuation of application No. 11/261,346, filed on Oct. 27, 2005, now abandoned, which is a continuation of application No. 09/830,144, filed as application No. PCT/JP99/05817 on Oct. 21, 1999, now Pat. No. 6,989,244.

(30) Foreign Application Priority Data

Oct. 21, 1998    (JP) .................................... 10-299962

(51) Int. Cl.
| C12Q 1/48 | (2006.01) |
| G01N 33/53 | (2006.01) |
| C12P 21/04 | (2006.01) |
| C12N 15/00 | (2006.01) |
| C12N 1/20 | (2006.01) |
| C07H 21/04 | (2006.01) |
| C07K 1/00 | (2006.01) |

(52) U.S. Cl. ......... 435/15; 435/7.2; 435/69.1; 435/71.1; 435/440; 435/252.3; 536/23.2; 530/350

(58) Field of Classification Search ........................ None
See application file for complete search history.

(56) References Cited

U.S. PATENT DOCUMENTS

| 5,580,723 | A | 12/1996 | Wells et al. |
| 5,837,819 | A | 11/1998 | Matsuomoto et al. |
| 5,945,301 | A | 8/1999 | Ueno et al. |
| 5,989,862 | A | 11/1999 | Matsuomoto et al. |
| 6,140,042 | A | 10/2000 | Matsuomoto et al. |
| 6,451,617 | B1 | 9/2002 | Ono et al. |
| 6,551,840 | B2 | 4/2003 | Ono et al. |
| 6,989,244 | B1 * | 1/2006 | Tsuchiya et al. ................. 435/15 |
| 2002/0119525 | A1 | 8/2002 | Matsuomoto et al. |
| 2003/0162228 | A1 | 8/2003 | Ono et al. |

FOREIGN PATENT DOCUMENTS

| EP | 0 803 571 A2 | 10/1997 |
| EP | 0 919 621 A1 | 6/1999 |
| JP | 10-4976 | 1/1998 |
| JP | 2000-197500 | 7/2000 |
| WO | WO 98/03663 A1 | 1/1998 |
| WO | PCT/JP98/04796 | 10/1998 |
| WO | WO 99/40202 | 8/1999 |

OTHER PUBLICATIONS

Fish & Richardson P.C., Preliminary Amendment in U.S. Appl. No. 09/830,144, filed Apr. 20, 2001 (8 pages).
Restriction Requirement in U.S. Appl. No. 09/830,144, mailed Sep. 27, 2002 (6 pages).
Fish & Richardson P.C., Response to Restriction Requirement in U.S. Appl. No. 09/830,144, filed Oct. 28, 2002 (2 pages).
Office Action in U.S. Appl. No. 09/830,144, mailed Dec. 27, 2002 (14 pages).
Fish & Richardson P.C., Reply to Office Action in U.S. Appl. No. 09/830,144, filed Jun. 27, 2003 (21 pages).
Final Office Action in U.S. Appl. No. 09/830,144, mailed Dec. 16, 2003 (25 pages).
Fish & Richardson P.C., Reply to Office Action in U.S. Appl. No. 09/830,144, filed Oct. 7, 2004 (14 pages).
Notice of Allowance and Notice of Allowability in U.S. Appl. No. 09/830,144, mailed Dec. 27, 2004 (7 pages).
Notice of Allowance and Notice of Allowability, in U.S. Appl. No. 09/830,144, mailed Aug. 12, 2005 (7 pages).
Fish & Richardson P.C., Preliminary Amendment in U.S. Appl. No. 09/830,144, filed May 6, 2005 (6 pages).
Fish & Richardson P.C., Response to Notice of Allowance, in U.S. Appl. No. 09/830,144, mailed Aug. 12, 2005, filed Oct. 27, 2005 (5 pages).
Fish & Richardson P.C., Preliminary Amendment, in U.S. Appl. No. 11/261,346, filed Oct. 27, 2005 (11 pages).
Office Action in U.S. Appl. No. 11/261,346, mailed Aug. 7, 2007 (34 pages).
Ausubel affinity purification of proteins binding to GST funsion proteins Section 20.2. Current Protocols in Molecular Biology, John Wiley and Sons (1996).
Bertelsen et al., TAB1 modulates IL-1alpha mediated cytokine secretion but it dispendable for TAK1 activation, Cell Signal., Mar. 2007; 19(3): 646-57. Epub Oct. 17, 2006.
Bowie, et al. (1990). Deciphering the message in protein sequences: tolerance to amino acid substitutions. Science. 247(4948):1306-1310.
Fields and Song (1989). A novel genetic system to detect protein-protein interactions. Nature. 340(6230):245-246.
Khaled, A.R., et al. (1998). Use of phosphorothioate-modified oligodeoxynucleotides to inhibit NF-κB expression and lymphocyte function. Clin Immunol Immunopathol. 86(2):170-179.
Kingsley (1994). The TGF-β superfamily: new members, new receptors, and new genetic tests of function in different organisms. Genes Dev. 8(2):133-146.
Kulkarni, et al. (1993). Transforming growth factor β1 null mutation in mice causes excessive inflammatory response and early death. Proc Natl Acad Sci USA. 15;90(2):770-774.

(Continued)

Primary Examiner — Yong Pak
(74) Attorney, Agent, or Firm — Fish & Richardson P.C.

(57) ABSTRACT

Revealed are that the actions of inflammatory cytokine and the production of inflammatory cytokines such as IL-1 and TNF induced by an inflammatory stimulus as well as the production of other inflammatory cytokines such as IL-6 induced by the former class of inflammatory cytokines are all suppressed by inhibiting the signal transduction through TAK1.

16 Claims, 5 Drawing Sheets

OTHER PUBLICATIONS

Letterio and Roberts (1998). Regulation of immune responses by TGF-β. Annu Rev Immunol. 16:137-161.

Maeda, et al. (1995). TGF-β enhances macrophage ability to produce IL-10 in normal and tumor-bearing mice. Immunol. 155(10):4926-4932.

Matsumoto (1998). Functional analysis of cancer-related genes in yeast system. Research Report Compilation on Priority Areas in the Cancer Research, pp. 720-723. Translated to English.

McCartney-Francis, et al. (1998). TGF-β: a balancing act. Int Rev Immunol. 16(5-6):553-580.

Metzler inhibition and activation of enzymes, competitive inhibitors. Biochemistry; The Chemical Reactions of Living Cells. Academic Press, Inc., New York, NY, pp. 315-316 (1977).

Ninomiya-Tsuji, et al. (1999). The kinase TAK1 can activate the NIK-I kappaB as well as the MAP kinase cascade in the IL-1 signaling pathway. Nature. 398(6724):252-256.

Palaparti, et al. (1997). The Groucho/transducin-like enhancer of split transcriptional repressors interact with the genetically defined amino-terminal silencing domain of histone H3. J Biol Chem. 272(42):26604-26610.

Phizichy et al., Protein-protein interactions: methods for detection and analysis, Microbiol Rev. Mar. 1995; 59(1): 94-123 Review.

Sakurai, et al. (1998). TGF-beta-activated kinase 1 stimulates NF-kappa B activation by an NF-kappa B-inducing kinase-independent mechanism. Biochem Biophys Res Commun. 243(2):545-549.

Sakurai, et al. (1999). Functional interactions of transforming growth factor beta-activated kinase 1 with IkappaB kinases to stimulate NF-kappaB activation. J Biol Chem. 274(15):10641-10648.

Sakurai, et al. (1999). Molecular mechanism of TAK1-induced NF-kB activation. Japanese Journal of Inflammation. 19(4):197-2002. Translated to English.

Shibuya, et al. (1996). TAB1: an activator of the TAK1 MAPKKK in TGF-β signal transduction. Science. 272(5265):1179-1182.

Shirakabe, et al. (1997). TAK1 mediates the ceramide signaling to stress-activated protein kinase/c-Jun N-terminal kinase. J Biol Chem. 272(13):8141-8144.

Swope and Huganir (1994). Binding of the nicotinic acetylcholine receptor to SH2 domains of Fyn and Fyk protein tyrosine kinases. J Biol Chem. 269(47):29817-29824.

Tsuji, et al. (1999). MAP kinase kinase kinase, TAK1, functions in IL-1 signaling pathway. Experimental Medicine. 17(10):1229-1232. Translated to English.

Wishart, et al. (1995). A single mutation converts a novel phosphotyrosine binding domain into a dual-specificity phosphatase. J Biol Chem. 270(45):26782-26785.

Witkowski, et al. (1999). Conversion of a β-ketoacyl synthase to a malonyl decarboxylase by replacement of the active-site cysteine with glutamine. Biochemistry. 38(36):11643-11650.

Yamaguchi (1995). Identification of a member of the MAPKKK family as a potential mediator of TGF-β signal transduction. Science. 270(5244):2008-2011.

Yao et al., "Interleukin-1 (IL-1)-induced TAK1-dependent *Versus* MEKK3-dependent NFκB Activation Pathways Bifurcate at IL-1 Receptor-associated Kinase Modification", J. Biol. Chem., vol. 282(9), pp. 6075-6089 (2007).

Hiscott et al., "Characterization of a Functional NF-κB Site in the Human Interleukin 1β Promoter: Evidence for a Positive Autoregulatory Loop", Molecular and Cellular Biology, vol. 13(10), pp. 6231-6240 (1993).

Saklatvala et al., "Protein kinase cascades in intracellular signaling by interleukin-I and tumour necrosis factor", Biochem. Soc. Symp., vol. 64, pp. 63-77 (1999).

Shakhov et al., "κB-Type Enhancers are Involved in Lipopolysaccharide-Mediated Transcriptional Activation of the Tumor Necrosis Factor α Gene in Primary Macrophages", J. Exp. Med., vol. 171(1), pp. 35-47 (1990).

De Cesaris et al., "Tumor Necrosis Factor-α Induces Interleukin-6 Production and Integrin Ligand Expression by Distinct Transduction Pathways", The Journal of Biological Chemistry, vol. 273, No. 13, pp. 7566-7571 (1998).

Goldstein et al., "TNF-induced IL-8 and MCP-1 production in the eosinophilic cell line, EOL-1", Mediators of Inflammation, vol. 5, pp. 218-223 (1996).

\* cited by examiner

| AMP $^r$ | : AMPICILLIN RESISTANT GENE |
| SV40 ori | : SV40 REPLICATION ORIGIN |
| β-globin | : RABBIT β-GLOBIN GENE |
| ori | : pBR REPLICATION ORIGIN |
| H-2L$^d$ | : MOUSE H-2L$^d$ PROMOTER |

1. pM/pVP16
2. pM-TAK1/pVP16
3. pM-TAK1/pVP16-C68
4. pM-TAK1DN/pVP16
5. pM-TAK1DN/pVP16-C68

SEQUENCE LISTING

```
<160> NUMBER OF SEQ ID NOS: 10

<210> SEQ ID NO 1
<211> LENGTH: 2656
<212> TYPE: DNA
<213> ORGANISM: Homo sapiens
```

-continued

```
<220> FEATURE:
<221> NAME/KEY: CDS
<222> LOCATION: (183)..(1919)

<400> SEQUENCE: 1
gtcgagatcc attgtgctct aaagacggct gtggccgctg cctctacccc cgccacggat      60
cgccgggtag taggactgcg cggctccagg ctgagggtcg gtccggaggc gggtgggcgc     120
gggtctcacc cggattgtcc gggtggcacc gttcccggcc ccaccgggcg ccgcgaggga     180 tc atg tct aca gcc tct gcc gcc tcc tcc tcc tcg tct tcg gcc            227
   Met Ser Thr Ala Ser Ala Ala Ser Ser Ser Ser Ser Ser Ala
   1               5                  10                  15 ggt gag atg atc gaa gcc cct tcc cag gtc ctc aac ttt gaa gag atc       275
Gly Glu Met Ile Glu Ala Pro Ser Gln Val Leu Asn Phe Glu Glu Ile
                20                  25                  30 gac tac aag gag atc gag gtg gaa gag gtt gtt gga aga gga gcc ttt       323
Asp Tyr Lys Glu Ile Glu Val Glu Glu Val Val Gly Arg Gly Ala Phe
            35                  40                  45 gga gtt gtt tgc aaa gct aag tgg aga gca aaa gat gtt gct att aaa       371
Gly Val Val Cys Lys Ala Lys Trp Arg Ala Lys Asp Val Ala Ile Lys
        50                  55                  60 caa ata gaa agt gaa tct gag agg aaa gcg ttt att gta gag ctt cgg       419
Gln Ile Glu Ser Glu Ser Glu Arg Lys Ala Phe Ile Val Glu Leu Arg
    65                  70                  75 cag tta tcc cgt gtg aac cat cct aat att gta aag ctt tat gga gcc       467
Gln Leu Ser Arg Val Asn His Pro Asn Ile Val Lys Leu Tyr Gly Ala
80                  85                  90                  95 tgc ttg aat cca gtg tgt ctt gtg atg gaa tat gct gaa ggg ggc tct       515
Cys Leu Asn Pro Val Cys Leu Val Met Glu Tyr Ala Glu Gly Gly Ser
                100                 105                 110 tta tat aat gtg ctg cat ggt gct gaa cca ttg cca tat tat act gct       563
Leu Tyr Asn Val Leu His Gly Ala Glu Pro Leu Pro Tyr Tyr Thr Ala
            115                 120                 125 gcc cac gca atg agt tgg tgt tta cag tgt tcc caa gga gtg gct tat       611
Ala His Ala Met Ser Trp Cys Leu Gln Cys Ser Gln Gly Val Ala Tyr
        130                 135                 140 ctt cac agc atg caa ccc aaa gcg cta att cac agg gac ctg aaa cca       659
Leu His Ser Met Gln Pro Lys Ala Leu Ile His Arg Asp Leu Lys Pro
    145                 150                 155 cca aac tta ctg ctg gtt gca ggg gga aca gtt cta aaa att tgt gat       707
Pro Asn Leu Leu Leu Val Ala Gly Gly Thr Val Leu Lys Ile Cys Asp
160                 165                 170                 175 ttt ggt aca gcc tgt gac att cag aca cac atg acc aat aac aag ggg       755
Phe Gly Thr Ala Cys Asp Ile Gln Thr His Met Thr Asn Asn Lys Gly
                180                 185                 190 agt gct gct tgg atg gca cct gaa gtt ttt gaa ggt agt aat tac agt       803
Ser Ala Ala Trp Met Ala Pro Glu Val Phe Glu Gly Ser Asn Tyr Ser
            195                 200                 205 gaa aaa tgt gac gtc ttc agc tgg ggt att att ctt tgg gaa gtg ata       851
Glu Lys Cys Asp Val Phe Ser Trp Gly Ile Ile Leu Trp Glu Val Ile
        210                 215                 220 acg cgt cgg aaa ccc ttt gat gag att ggt ggc cca gct ttc cga atc       899
Thr Arg Arg Lys Pro Phe Asp Glu Ile Gly Gly Pro Ala Phe Arg Ile
    225                 230                 235 atg tgg gct gtt cat aat ggt act cga cca cca ctg ata aaa aat tta       947
Met Trp Ala Val His Asn Gly Thr Arg Pro Pro Leu Ile Lys Asn Leu
240                 245                 250                 255 cct aag ccc att gag agc ctg atg act cgt tgt tgg tct aaa gat cct       995
Pro Lys Pro Ile Glu Ser Leu Met Thr Arg Cys Trp Ser Lys Asp Pro
                260                 265                 270
```

```
tcc cag cgc cct tca atg gag gaa att gtg aaa ata atg act cac ttg   1043
Ser Gln Arg Pro Ser Met Glu Glu Ile Val Lys Ile Met Thr His Leu
            275                 280                 285 atg cgg tac ttt cca gga gca gat gag cca tta cag tat cct tgt cag   1091
Met Arg Tyr Phe Pro Gly Ala Asp Glu Pro Leu Gln Tyr Pro Cys Gln
        290                 295                 300 tat tca gat gaa gga cag agc aac tct gcc acc agt aca ggc tca ttc   1139
Tyr Ser Asp Glu Gly Gln Ser Asn Ser Ala Thr Ser Thr Gly Ser Phe
    305                 310                 315 atg gac att gct tct aca aat acg agt aac aaa agt gac act aat atg   1187
Met Asp Ile Ala Ser Thr Asn Thr Ser Asn Lys Ser Asp Thr Asn Met
320                 325                 330                 335 gag caa gtt cct gcc aca aat gat act att aag cgc tta gaa tca aaa   1235
Glu Gln Val Pro Ala Thr Asn Asp Thr Ile Lys Arg Leu Glu Ser Lys
                340                 345                 350 ttg ttg aaa aat cag gca aag caa cag agt gaa tct gga cgt tta agc   1283
Leu Leu Lys Asn Gln Ala Lys Gln Gln Ser Glu Ser Gly Arg Leu Ser
            355                 360                 365 ttg gga gcc tcc cat ggg agc agt gtg gag agc ttg ccc cca acc tct   1331
Leu Gly Ala Ser His Gly Ser Ser Val Glu Ser Leu Pro Pro Thr Ser
        370                 375                 380 gag ggc aag agg atg agt gct gac atg tct gaa ata gaa gct agg atc   1379
Glu Gly Lys Arg Met Ser Ala Asp Met Ser Glu Ile Glu Ala Arg Ile
    385                 390                 395 gcc gca acc aca ggc aac gga cag cca aga cgt aga tcc atc caa gac   1427
Ala Ala Thr Thr Gly Asn Gly Gln Pro Arg Arg Arg Ser Ile Gln Asp
400                 405                 410                 415 ttg act gta act gga aca gaa cct ggt cag gtg agc agt agg tca tcc   1475
Leu Thr Val Thr Gly Thr Glu Pro Gly Gln Val Ser Ser Arg Ser Ser
                420                 425                 430 agt ccc agt gtc aga atg att act acc tca gga cca acc tca gaa aag   1523
Ser Pro Ser Val Arg Met Ile Thr Thr Ser Gly Pro Thr Ser Glu Lys
            435                 440                 445 cca act cga agt cat cca tgg acc cct gat gat tcc aca gat acc aat   1571
Pro Thr Arg Ser His Pro Trp Thr Pro Asp Asp Ser Thr Asp Thr Asn
        450                 455                 460 gga tca gat aac tcc atc cca atg gct tat ctt aca ctg gat cac caa   1619
Gly Ser Asp Asn Ser Ile Pro Met Ala Tyr Leu Thr Leu Asp His Gln
    465                 470                 475 cta cag cct cta gca ccg tgc cca aac tcc aaa gaa tct atg gca gtg   1667
Leu Gln Pro Leu Ala Pro Cys Pro Asn Ser Lys Glu Ser Met Ala Val
480                 485                 490                 495 ttt gaa cag cat tgt aaa atg gca caa gaa tat atg aaa gtt caa aca   1715
Phe Glu Gln His Cys Lys Met Ala Gln Glu Tyr Met Lys Val Gln Thr
                500                 505                 510 gaa att gca ttg tta tta cag aga aag caa gaa cta gtt gca gaa ctg   1763
Glu Ile Ala Leu Leu Leu Gln Arg Lys Gln Glu Leu Val Ala Glu Leu
            515                 520                 525 gac cag gat gaa aag gac cag caa aat aca tct cgc ctg gta cag gaa   1811
Asp Gln Asp Glu Lys Asp Gln Gln Asn Thr Ser Arg Leu Val Gln Glu
        530                 535                 540 cat aaa aag ctt tta gat gaa aac aaa agc ctt tct act tac tac cag   1859
His Lys Lys Leu Leu Asp Glu Asn Lys Ser Leu Ser Thr Tyr Tyr Gln
    545                 550                 555 caa tgc aaa aaa caa cta gag gtc atc aga agt cag cag cag aaa cga   1907
Gln Cys Lys Lys Gln Leu Glu Val Ile Arg Ser Gln Gln Gln Lys Arg
560                 565                 570                 575 caa ggc act tca tgattctctg ggaccgttac attttgaaat atgcaaagaa        1959
Gln Gly Thr Ser agacttttt tttaaggaaa ggaaaacctt ataatgacga ttcatgagtg ttagcttttt   2019
```

-continued

```
ggcgtgttct gaatgccaac tgcctatatt tgctgcattt ttttcattgt ttattttcct    2079
tttctcatgg tggacataca attttactgt tcattgcat aacatggtag catctgtgac     2139
ttgaatgagc agcactttgc aacttcaaaa cagatgcagt gaactgtggc tgtatatgca    2199
tgctcattgt gtgaaggcta gcctaacaga acaggaggta tcaaactagc tgctatgtgc    2259
aaacagcgtc cattttttca tattagaggt ggaacctcaa gaatgacttt attcttgtat    2319
ctcatctcaa atattaata attttttttcc caaaagatgg tatataccaa gttaaagaca    2379
gggtattata aatttagagt gattggtggt atattacgga aatacggaac ctttagggat    2439
agttccgtgt aagggctttg atgccagcat ccttggatca gtactgaact cagttccatc    2499
cgtaaaatat gtaaaggtaa gtggcagctg ctctatttaa tgaaagcagt tttaccggat    2559
tttgttagac taaaatttga ttgtgataca ttgaacaaaa tggaactcat ttttttttaag   2619 gagtaaagat tttctttaga gcacaatgga tctcgac                             2656
```

<210> SEQ ID NO 2
<211> LENGTH: 579
<212> TYPE: PRT
<213> ORGANISM: Homo sapiens

<400> SEQUENCE: 2

```
Met Ser Thr Ala Ser Ala Ala Ser Ser Ser Ser Ser Ser Ala Gly
  1               5                  10                  15

Glu Met Ile Glu Ala Pro Ser Gln Val Leu Asn Phe Glu Glu Ile Asp
                 20                  25                  30

Tyr Lys Glu Ile Glu Val Glu Val Val Gly Arg Gly Ala Phe Gly
             35                  40                  45

Val Val Cys Lys Ala Lys Trp Arg Ala Lys Asp Val Ala Ile Lys Gln
 50                  55                  60

Ile Glu Ser Glu Ser Glu Arg Lys Ala Phe Ile Val Glu Leu Arg Gln
 65                  70                  75                  80

Leu Ser Arg Val Asn His Pro Asn Ile Val Lys Leu Tyr Gly Ala Cys
                 85                  90                  95

Leu Asn Pro Val Cys Leu Val Met Glu Tyr Ala Glu Gly Gly Ser Leu
            100                 105                 110

Tyr Asn Val Leu His Gly Ala Glu Pro Leu Pro Tyr Tyr Thr Ala Ala
            115                 120                 125

His Ala Met Ser Trp Cys Leu Gln Cys Ser Gln Gly Val Ala Tyr Leu
            130                 135                 140

His Ser Met Gln Pro Lys Ala Leu Ile His Arg Asp Leu Lys Pro Pro
145                 150                 155                 160

Asn Leu Leu Leu Val Ala Gly Gly Thr Val Leu Lys Ile Cys Asp Phe
                165                 170                 175

Gly Thr Ala Cys Asp Ile Gln Thr His Met Thr Asn Asn Lys Gly Ser
            180                 185                 190

Ala Ala Trp Met Ala Pro Glu Val Phe Glu Gly Ser Asn Tyr Ser Glu
            195                 200                 205

Lys Cys Asp Val Phe Ser Trp Gly Ile Ile Leu Trp Glu Val Ile Thr
            210                 215                 220

Arg Arg Lys Pro Phe Asp Glu Ile Gly Gly Pro Ala Phe Arg Ile Met
225                 230                 235                 240

Trp Ala Val His Asn Gly Thr Arg Pro Pro Leu Ile Lys Asn Leu Pro
                245                 250                 255

Lys Pro Ile Glu Ser Leu Met Thr Arg Cys Trp Ser Lys Asp Pro Ser
```

```
                    260                 265                 270
Gln Arg Pro Ser Met Glu Glu Ile Val Lys Ile Met Thr His Leu Met
            275                 280                 285
Arg Tyr Phe Pro Gly Ala Asp Glu Pro Leu Gln Tyr Pro Cys Gln Tyr
        290                 295                 300
Ser Asp Glu Gly Gln Ser Asn Ser Ala Thr Ser Thr Gly Ser Phe Met
305                 310                 315                 320
Asp Ile Ala Ser Thr Asn Thr Ser Asn Lys Ser Asp Thr Asn Met Glu
                325                 330                 335
Gln Val Pro Ala Thr Asn Asp Thr Ile Lys Arg Leu Glu Ser Lys Leu
            340                 345                 350
Leu Lys Asn Gln Ala Lys Gln Gln Ser Glu Ser Gly Arg Leu Ser Leu
        355                 360                 365
Gly Ala Ser His Gly Ser Ser Val Glu Ser Leu Pro Pro Thr Ser Glu
    370                 375                 380
Gly Lys Arg Met Ser Ala Asp Met Ser Glu Ile Glu Ala Arg Ile Ala
385                 390                 395                 400
Ala Thr Thr Gly Asn Gly Gln Pro Arg Arg Arg Ser Ile Gln Asp Leu
                405                 410                 415
Thr Val Thr Gly Thr Glu Pro Gly Gln Val Ser Ser Arg Ser Ser Ser
            420                 425                 430
Pro Ser Val Arg Met Ile Thr Thr Ser Gly Pro Thr Ser Glu Lys Pro
        435                 440                 445
Thr Arg Ser His Pro Trp Thr Pro Asp Asp Ser Thr Asp Thr Asn Gly
    450                 455                 460
Ser Asp Asn Ser Ile Pro Met Ala Tyr Leu Thr Leu Asp His Gln Leu
465                 470                 475                 480
Gln Pro Leu Ala Pro Cys Pro Asn Ser Lys Glu Ser Met Ala Val Phe
                485                 490                 495
Glu Gln His Cys Lys Met Ala Gln Glu Tyr Met Lys Val Gln Thr Glu
            500                 505                 510
Ile Ala Leu Leu Leu Gln Arg Lys Gln Glu Leu Val Ala Glu Leu Asp
        515                 520                 525
Gln Asp Glu Lys Asp Gln Gln Asn Thr Ser Arg Leu Val Gln Glu His
    530                 535                 540
Lys Lys Leu Leu Asp Glu Asn Lys Ser Leu Ser Thr Tyr Tyr Gln Gln
545                 550                 555                 560
Cys Lys Lys Gln Leu Glu Val Ile Arg Ser Gln Gln Gln Lys Arg Gln
                565                 570                 575
Gly Thr Ser

<210> SEQ ID NO 3
<211> LENGTH: 1560
<212> TYPE: DNA
<213> ORGANISM: Homo sapiens
<220> FEATURE:
<221> NAME/KEY: CDS
<222> LOCATION: (30)..(1541)

<400> SEQUENCE: 3
gaattcgtgg cccgcagggt tcctccaag atg gcg gcg cag agg agg agc ttg    53
                                Met Ala Ala Gln Arg Arg Ser Leu
                                                      5 ctg cag agt gag cag cag cca agc tgg aca gat gac ctg cct ctc tgc   101
Leu Gln Ser Glu Gln Gln Pro Ser Trp Thr Asp Asp Leu Pro Leu Cys
    10                  15                  20
```

| | | | | | | | | | | | | | | | | |
|---|---|---|---|---|---|---|---|---|---|---|---|---|---|---|---|---|
| cac | ctc | tct | ggg | gtt | ggc | tca | gcc | tcc | aac | cgc | agc | tac | tct | gct | gat | 149 |
| His | Leu | Ser | Gly | Val | Gly | Ser | Ala | Ser | Asn | Arg | Ser | Tyr | Ser | Ala | Asp | |
| 25 | | | | 30 | | | | | 35 | | | | | 40 | | |
| ggc | aag | ggc | act | gag | agc | cac | ccg | cca | gag | gac | agc | tgg | ctc | aag | ttc | 197 |
| Gly | Lys | Gly | Thr | Glu | Ser | His | Pro | Pro | Glu | Asp | Ser | Trp | Leu | Lys | Phe | |
| | | | | 45 | | | | | 50 | | | | | 55 | | |
| agg | agt | gag | aac | aac | tgc | ttc | ctg | tat | ggg | gtc | ttc | aac | ggc | tat | gat | 245 |
| Arg | Ser | Glu | Asn | Asn | Cys | Phe | Leu | Tyr | Gly | Val | Phe | Asn | Gly | Tyr | Asp | |
| | | | 60 | | | | | 65 | | | | | 70 | | | |
| ggc | aac | cga | gtg | acc | aac | ttc | gtg | gcc | cag | cgg | ctg | tcc | gca | gag | ctc | 293 |
| Gly | Asn | Arg | Val | Thr | Asn | Phe | Val | Ala | Gln | Arg | Leu | Ser | Ala | Glu | Leu | |
| | | 75 | | | | | 80 | | | | | 85 | | | | |
| ctg | ctg | ggc | cag | ctg | aat | gcc | gag | cac | gcc | gag | gcc | gat | gtg | cgg | cgt | 341 |
| Leu | Leu | Gly | Gln | Leu | Asn | Ala | Glu | His | Ala | Glu | Ala | Asp | Val | Arg | Arg | |
| | 90 | | | | | 95 | | | | | 100 | | | | | |
| gtg | ctg | ctg | cag | gcc | ttc | gat | gtg | gtg | gag | agg | agc | ttc | ctg | gag | tcc | 389 |
| Val | Leu | Leu | Gln | Ala | Phe | Asp | Val | Val | Glu | Arg | Ser | Phe | Leu | Glu | Ser | |
| 105 | | | | | 110 | | | | | 115 | | | | | 120 | |
| att | gac | gac | gcc | ttg | gct | gag | aag | gca | agc | ctc | cag | tcg | caa | ttg | cca | 437 |
| Ile | Asp | Asp | Ala | Leu | Ala | Glu | Lys | Ala | Ser | Leu | Gln | Ser | Gln | Leu | Pro | |
| | | | | 125 | | | | | 130 | | | | | 135 | | |
| gag | gga | gtc | cct | cag | cac | cag | ctg | cct | cct | cag | tat | cag | aag | atc | ctt | 485 |
| Glu | Gly | Val | Pro | Gln | His | Gln | Leu | Pro | Pro | Gln | Tyr | Gln | Lys | Ile | Leu | |
| | | | 140 | | | | | 145 | | | | | 150 | | | |
| gag | aga | ctc | aag | acg | tta | gag | agg | gaa | att | tcg | gga | ggg | gcc | atg | gcc | 533 |
| Glu | Arg | Leu | Lys | Thr | Leu | Glu | Arg | Glu | Ile | Ser | Gly | Gly | Ala | Met | Ala | |
| | | 155 | | | | | 160 | | | | | 165 | | | | |
| gtt | gtg | gcg | gtc | ctt | ctc | aac | aac | aag | ctc | tac | gtc | gcc | aat | gtc | ggt | 581 |
| Val | Val | Ala | Val | Leu | Leu | Asn | Asn | Lys | Leu | Tyr | Val | Ala | Asn | Val | Gly | |
| | 170 | | | | | 175 | | | | | 180 | | | | | |
| aca | aac | cgt | gca | ctt | tta | tgc | aaa | tcg | aca | gtg | gat | ggg | ttg | cag | gtg | 629 |
| Thr | Asn | Arg | Ala | Leu | Leu | Cys | Lys | Ser | Thr | Val | Asp | Gly | Leu | Gln | Val | |
| 185 | | | | | 190 | | | | | 195 | | | | | 200 | |
| aca | cag | ctg | aac | gtg | gac | cac | acc | aca | gag | aac | gag | gat | gag | ctc | ttc | 677 |
| Thr | Gln | Leu | Asn | Val | Asp | His | Thr | Thr | Glu | Asn | Glu | Asp | Glu | Leu | Phe | |
| | | | | 205 | | | | | 210 | | | | | 215 | | |
| cgt | ctt | tcg | cag | ctg | ggc | ttg | gat | gct | gga | aag | atc | aag | cag | gtg | ggg | 725 |
| Arg | Leu | Ser | Gln | Leu | Gly | Leu | Asp | Ala | Gly | Lys | Ile | Lys | Gln | Val | Gly | |
| | | | 220 | | | | | 225 | | | | | 230 | | | |
| atc | atc | tgt | ggg | cag | gag | agc | acc | cgg | cgg | atc | ggg | gat | tac | aag | gtt | 773 |
| Ile | Ile | Cys | Gly | Gln | Glu | Ser | Thr | Arg | Arg | Ile | Gly | Asp | Tyr | Lys | Val | |
| | | 235 | | | | | 240 | | | | | 245 | | | | |
| aaa | tat | ggc | tac | acg | gac | att | gac | ctt | ctc | agc | gct | gcc | aag | tcc | aaa | 821 |
| Lys | Tyr | Gly | Tyr | Thr | Asp | Ile | Asp | Leu | Leu | Ser | Ala | Ala | Lys | Ser | Lys | |
| | 250 | | | | | 255 | | | | | 260 | | | | | |
| cca | atc | atc | gca | gag | cca | gaa | atc | cat | ggg | gca | cag | ccg | ctg | gat | ggg | 869 |
| Pro | Ile | Ile | Ala | Glu | Pro | Glu | Ile | His | Gly | Ala | Gln | Pro | Leu | Asp | Gly | |
| 265 | | | | | 270 | | | | | 275 | | | | | 280 | |
| gtg | acg | ggc | ttc | ttg | gtg | ctg | atg | tcg | gag | ggg | ttg | tac | aag | gcc | cta | 917 |
| Val | Thr | Gly | Phe | Leu | Val | Leu | Met | Ser | Glu | Gly | Leu | Tyr | Lys | Ala | Leu | |
| | | | | 285 | | | | | 290 | | | | | 295 | | |
| gag | gca | gcc | cat | ggg | cct | ggg | cag | gcc | aac | cag | gag | att | gct | gcg | atg | 965 |
| Glu | Ala | Ala | His | Gly | Pro | Gly | Gln | Ala | Asn | Gln | Glu | Ile | Ala | Ala | Met | |
| | | | 300 | | | | | 305 | | | | | 310 | | | |
| att | gac | act | gag | ttt | gcc | aag | cag | acc | tcc | ctg | gac | gca | gtg | gcc | cag | 1013 |
| Ile | Asp | Thr | Glu | Phe | Ala | Lys | Gln | Thr | Ser | Leu | Asp | Ala | Val | Ala | Gln | |
| | | 315 | | | | | 320 | | | | | 325 | | | | |
| gcc | gtc | gtg | gac | cgg | gtg | aag | cgc | atc | cac | agc | gac | acc | ttc | gcc | agt | 1061 |
| Ala | Val | Val | Asp | Arg | Val | Lys | Arg | Ile | His | Ser | Asp | Thr | Phe | Ala | Ser | |
| | 330 | | | | | 335 | | | | | 340 | | | | | |

| | | | | | | | | | | | | |
|---|---|---|---|---|---|---|---|---|---|---|---|---|
| ggt | ggg | gag | cgt | gcc | agg | ttc | tgc | ccc | cgg | cac | gag | gac atg acc ctg | 1109 |
| Gly | Gly | Glu | Arg | Ala | Arg | Phe | Cys | Pro | Arg | His | Glu | Asp Met Thr Leu |
| 345 | | | | 350 | | | | | 355 | | | 360 |

```
ggt ggg gag cgt gcc agg ttc tgc ccc cgg cac gag gac atg acc ctg    1109
Gly Gly Glu Arg Ala Arg Phe Cys Pro Arg His Glu Asp Met Thr Leu
345                 350                 355                 360 cta gtg agg aac ttt ggc tac ccg ctg ggc gaa atg agc cag ccc aca    1157
Leu Val Arg Asn Phe Gly Tyr Pro Leu Gly Glu Met Ser Gln Pro Thr
            365                 370                 375 ccg agc cca gcc cca gct gca gga gga cga gtg tac cct gtg tct gtg    1205
Pro Ser Pro Ala Pro Ala Ala Gly Gly Arg Val Tyr Pro Val Ser Val
        380                 385                 390 cca tac tcc agc gcc cag agc acc agc aag acc agc gtg acc ctc tcc    1253
Pro Tyr Ser Ser Ala Gln Ser Thr Ser Lys Thr Ser Val Thr Leu Ser
        395                 400                 405 ctt gtc atg ccc tcc cag ggc cag atg gtc aac ggg gct cac agt gct    1301
Leu Val Met Pro Ser Gln Gly Gln Met Val Asn Gly Ala His Ser Ala
    410                 415                 420 tcc acc ctg gac gaa gcc acc ccc acc ctc acc aac caa agc ccg acc    1349
Ser Thr Leu Asp Glu Ala Thr Pro Thr Leu Thr Asn Gln Ser Pro Thr
425                 430                 435                 440 tta acc ctg cag tcc acc aac acg cac acg cag agc agc agc tcc agc    1397
Leu Thr Leu Gln Ser Thr Asn Thr His Thr Gln Ser Ser Ser Ser Ser
            445                 450                 455 tct gac gga ggc ctc ttc cgc tcc cgg ccc gcc cac tcg ctc ccg cct    1445
Ser Asp Gly Gly Leu Phe Arg Ser Arg Pro Ala His Ser Leu Pro Pro
        460                 465                 470 ggc gag gac ggt cgt gtt gag ccc tat gtg gac ttt gct gag ttt tac    1493
Gly Glu Asp Gly Arg Val Glu Pro Tyr Val Asp Phe Ala Glu Phe Tyr
        475                 480                 485 cgc ctc tgg agc gtg gac cat ggc gag cag agc gtg gtg aca gca ccg    1541
Arg Leu Trp Ser Val Asp His Gly Glu Gln Ser Val Val Thr Ala Pro
    490                 495                 500 tagggcagcc ggaggaatg                                                1560
```

<210> SEQ ID NO 4
<211> LENGTH: 504
<212> TYPE: PRT
<213> ORGANISM: Homo sapiens

<400> SEQUENCE: 4

```
Met Ala Ala Gln Arg Arg Ser Leu Leu Gln Ser Glu Gln Gln Pro Ser
                5                   10                  15

Trp Thr Asp Asp Leu Pro Leu Cys His Leu Ser Gly Val Gly Ser Ala
            20                  25                  30

Ser Asn Arg Ser Tyr Ser Ala Asp Gly Lys Gly Thr Glu Ser His Pro
        35                  40                  45

Pro Glu Asp Ser Trp Leu Lys Phe Arg Ser Glu Asn Asn Cys Phe Leu
    50                  55                  60

Tyr Gly Val Phe Asn Gly Tyr Asp Gly Asn Arg Val Thr Asn Phe Val
65                  70                  75                  80

Ala Gln Arg Leu Ser Ala Glu Leu Leu Leu Gly Gln Leu Asn Ala Glu
                85                  90                  95

His Ala Glu Ala Asp Val Arg Arg Val Leu Leu Gln Ala Phe Asp Val
            100                 105                 110

Val Glu Arg Ser Phe Leu Glu Ser Ile Asp Asp Ala Leu Ala Glu Lys
        115                 120                 125

Ala Ser Leu Gln Ser Gln Leu Pro Glu Gly Val Pro Gln His Gln Leu
    130                 135                 140

Pro Pro Gln Tyr Gln Lys Ile Leu Glu Arg Leu Lys Thr Leu Glu Arg
145                 150                 155                 160
```

-continued

Glu Ile Ser Gly Gly Ala Met Ala Val Val Ala Val Leu Leu Asn Asn
            165                 170                 175
Lys Leu Tyr Val Ala Asn Val Gly Thr Asn Arg Ala Leu Leu Cys Lys
                180                 185                 190
Ser Thr Val Asp Gly Leu Gln Val Thr Gln Leu Asn Val Asp His Thr
            195                 200                 205
Thr Glu Asn Glu Asp Glu Leu Phe Arg Leu Ser Gln Leu Gly Leu Asp
        210                 215                 220
Ala Gly Lys Ile Lys Gln Val Gly Ile Ile Cys Gly Gln Glu Ser Thr
225                 230                 235                 240
Arg Arg Ile Gly Asp Tyr Lys Val Lys Tyr Gly Tyr Thr Asp Ile Asp
                245                 250                 255
Leu Leu Ser Ala Ala Lys Ser Lys Pro Ile Ile Ala Glu Pro Glu Ile
            260                 265                 270
His Gly Ala Gln Pro Leu Asp Gly Val Thr Gly Phe Leu Val Leu Met
        275                 280                 285
Ser Glu Gly Leu Tyr Lys Ala Leu Glu Ala Ala His Gly Pro Gly Gln
    290                 295                 300
Ala Asn Gln Glu Ile Ala Ala Met Ile Asp Thr Glu Phe Ala Lys Gln
305                 310                 315                 320
Thr Ser Leu Asp Ala Val Ala Gln Ala Val Asp Arg Val Lys Arg
                325                 330                 335
Ile His Ser Asp Thr Phe Ala Ser Gly Glu Arg Ala Arg Phe Cys
            340                 345                 350
Pro Arg His Glu Asp Met Thr Leu Leu Val Arg Asn Phe Gly Tyr Pro
        355                 360                 365
Leu Gly Glu Met Ser Gln Pro Thr Pro Ser Pro Ala Pro Ala Ala Gly
    370                 375                 380
Gly Arg Val Tyr Pro Val Ser Val Pro Tyr Ser Ser Ala Gln Ser Thr
385                 390                 395                 400
Ser Lys Thr Ser Val Thr Leu Ser Leu Val Met Pro Ser Gln Gly Gln
                405                 410                 415
Met Val Asn Gly Ala His Ser Ala Ser Thr Leu Asp Glu Ala Thr Pro
            420                 425                 430
Thr Leu Thr Asn Gln Ser Pro Thr Leu Thr Leu Gln Ser Thr Asn Thr
        435                 440                 445
His Thr Gln Ser Ser Ser Ser Ser Asp Gly Gly Leu Phe Arg Ser
    450                 455                 460
Arg Pro Ala His Ser Leu Pro Pro Gly Glu Asp Gly Arg Val Glu Pro
465                 470                 475                 480
Tyr Val Asp Phe Ala Glu Phe Tyr Arg Leu Trp Ser Val Asp His Gly
                485                 490                 495
Glu Gln Ser Val Val Thr Ala Pro
            500

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 5
ccggaattcc accatggagc ttcggcagtt atcc         34

```
<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 6
ccggaattcc tactgacaag gatactgt                                    28

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 7
gtacttcagc acagttttag agaac                                       25

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 8
ggttgcatgc tgtgaaga                                               18

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 9
cggaattcga gctccggcag tgtcgcg                                     27

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:
      Artificially Synthesized Primer Sequence

<400> SEQUENCE: 10
aactgcaggc tactgacaag gatactgtaa                                  30
```

METHODS OF SCREENING COMPOUNDS INHIBITING SIGNAL TRANSDUCTION THROUGH INFLAMMATORY CYTOKINES

RELATED APPLICATIONS

This application is a continuation of U.S. patent application Ser. No. 11/261,346, filed Oct. 27, 2005, which is a continuation of U.S. patent application Ser. No. 09/830,144, filed Apr. 20, 2001, which is now U.S. Pat. No. 6,989,244, which is the national stage of International Application No. PCT/JP99/05817, filed Oct. 21, 1999, which claims priority to Japanese Patent Application No. 10/299962, filed Oct. 21, 1998. The entire disclosure of each of the above applications is hereby incorporated by reference.

TECHNICAL FIELD

The present invention relates to a method for screening compounds inhibiting signal transduction through inflammatory cytokines. The present invention also relates to the compound that can be isolated by the screening method and the use thereof. The present invention further relates to an inhibitor of the signal transduction through inflammatory cytokines, for example, inhibitors of the action and production of inflammatory cytokines, and anti-inflammatory agent, which contain as an active ingredient a compound inhibiting the signal transduction through TAK1.

BACKGROUND ART

The system of mitogen-activated protein kinase (MAPK) is known as a system involved in intracellular signal transduction.

MAPK system is a conserved eukaryotic signal transduction system, by which the receptor-mediated signals are converted to a variety of actions. MAPK system contains three types of protein kinases, namely, mitogen-activated protein kinase kinase kinase (MAPKKK), mitogen-activated protein kinase kinase (MAPKK), and mitogen-activated protein kinase (MAPK). MAPKK phosphorylates and activates MAPK, and MAPKKK phosphorylates and activates MAPKK (Nishida, E. et al., Trends Biochem. Sci. (1993) 18, 128; Blumer, K. J. et al., Trends Biochem. Sci. (1993) 19, 236; David R. J. et al., Trends Biochem. Sci. (1993) 19, 470; Marchall, C. J. et al., Cell (1995) 80, 179).

TGF-β-activated kinase 1 (TAK1), a member of the MAPKKK family, functions in the intracellular signal transduction system. The TAK1 protein was identified by Yamaguchi, K. et al. (Yamaguchi, K. et al., Science (1995) 270, 2008). The protein has been revealed to be involved in the signal transduction of TGF-β and to be activated by TGF-β.

TAK1 binding protein 1 (TAB1) binds to TAK1 and participates in the signal transduction system of TGF-β that activates TAK1. The TAB1 protein was identified by Shibuya, H. et al. (Shibuya, H. et al., Science (1996) 272, 1179-1182). TAB1 binds to TAK1 and activates the kinase activity of TAK1, thereby transducing the TGF-β signal.

A very recent report describes that TAK1 is also activated by tumor necrosis factor (TNF) and interleukin-1 (IL-1) (Shirakabe, K. et al., J. Biol. Chem. (1997) 272, 8141). It has also been reported that the activation of transcription factor NF-κB is induced after TAK1 activation (Moriguchi, T., et al., J. Biol. Chem. (1996) 271, 13675; Ponton, A., et al., J. Biol. Chem. (1996) 271, 8991; Sakurai S., et al., Biochem. Biophys. Res. Commun. (1998) 243, 545).

However, it is not at all known that the inhibition of signal transduction through TAK1 actually results in the inhibition of cellular responses to the inflammatory stimulation such as LPS or cytokine stimulation, for example, the inhibition of signal transduction through an inflammatory cytokine as an inflammatory mediator as well as results in the inhibition of inflammatory cytokine actions and further the inhibition of inflammatory cytokine production.

DISCLOSURE OF THE INVENTION

The present invention provides a method for screening compounds inhibiting TAK1-associated signal transduction of inflammatory cytokines. The present invention also provides compounds which can be isolated by the screening method and the uses thereof. The present invention further provides inhibitors of the signal transduction through inflammatory cytokines, which contain as an active ingredient a compound inhibiting the signal transduction through TAK1, for example, inhibitors of the action and production of inflammatory cytokines, and anti-inflammatory agents.

The present invention has revealed that the inhibition of signal transduction through TAK1 leads to the inhibition of inflammatory cytokine actions, further the inhibition of production of inflammatory cytokines such as IL-1 and TNF, of which production is induced by inflammatory stimulation, and also the inhibition of production of other inflammatory cytokines such as IL-6, of which production is induced by the inflammatory cytokines. The present invention was based on this finding.

Accordingly, the present invention provides:

(1) a method for screening compounds inhibiting signal transduction through inflammatory cytokines, the method comprising the steps of:
(a) contacting a test sample with TAK1 and TAB1;
(b) detecting binding between the TAK1 and the TAB1; and
(c) selecting a compound inhibiting the binding;

(2) the method of (1), wherein the TAK1 and or the TAB1 is fused with a peptide;

(3) the method of (1) or (2), wherein the TAK1 or the TAB1 is linked to a support;

(4) the method of any one of (1) to (3), wherein a label is attached to the TAK1 or the TAB1 and wherein the binding is detected by detecting or measuring the label;

(5) the method of any one of (1) to (3), wherein the binding is detected by detecting or measuring the TAB1 bound to TAK1 with a primary antibody against TAB1 or a primary antibody against the peptide fused with TAB1;

(6) the method of any one of (1) to (3), wherein the binding is detected by detecting or measuring the TAK1 bound to the TAB1 with a primary antibody against TAK1 or a primary antibody against the peptide fused with the TAK1;

(7) the method of any one of (1) to (3), wherein the binding is detected by detecting or measuring the TAB1 bound to the TAK1 with a primary antibody against TAB1 or a primary antibody against the peptide fused with TAB1, and a secondary antibody against the primary antibody;

(8) the method of any one of (1) to (3), wherein the binding is detected by detecting or measuring the TAK1 bound to the TAB1 with a primary antibody against TAK1 or a primary antibody against the peptide fused with the TAK1, and a secondary antibody against the primary antibody;

(9) the method of any one of (5) to (8), wherein the primary antibody or the secondary antibody is labeled with radioisotope, enzyme, or fluorescent substance;

(10) the method of (2), wherein the binding is detected with, as an index, change in the expression level of a reporter gene which is activated in response to the binding;

(11) the method of (10), wherein the reporter gene is luciferase, chloramphenicol acetyltransferase, green fluorescent protein, or β-galactosidase;

(12) a method for screening compounds inhibiting signal transduction through inflammatory cytokines, the method comprising the steps of:
(a) contacting a test sample with TAK1;
(b) detecting phosphorylation by the TAK1; and
(c) selecting a compound inhibiting the phosphorylation;

(13) a method for screening compounds inhibiting signal transduction through inflammatory cytokines, the method comprising the steps of:
(a) contacting a test sample with TAK1 and TAB1;
(b) detecting phosphorylation by the TAK1; and
(c) selecting a compound inhibiting the phosphorylation;

(14) the method of (12) or (13), wherein a substrate for the TAK1 is added and wherein the phosphorylation of the substrate by the TAK1 is detected;

(15) the method of (14), wherein the substrate for the TAK1 is MKK6 and/or MKK3;

(16) the method of any one of (12) to (15), wherein the TAK1 is fused with a peptide;

(17) the method of any one of (12) to (16), wherein the TAK1 is linked to a support;

(18) a method for screening compounds inhibiting signal transduction through inflammatory cytokines, the method comprising the steps of:
(a) introducing a test sample into and/or contacting the sample with cells expressing TAK1;
(b) detecting and/or measuring a biological activity transduced through the TAK1; and
(c) selecting a compound reducing the biological activity;

(19) the method of (18), wherein the biological activity is a biological activity of inflammatory cytokines;

(20) the method of (18), wherein the biological activity is detected with, as an index, change in the expression level of a reporter gene which is activated in response to the activity;

(21) a method for screening compounds inhibiting signal transduction through inflammatory cytokines, the method comprising the steps of:
(a) introducing a test sample into and/or contacting the sample with cells expressing TAK1 and TAB1;
(b) detecting and/or measuring a biological activity transduced through the TAK1 and the TAB1; and
(c) selecting a compound reducing the biological activity;

(22) the method of (21), wherein the biological activity is a biological activity of IL-1 or TNF;

(23) the method of (21), wherein the biological activity is detected with, as an index, change in the expression level of a reporter gene which is activated in response to the activity;

(24) the method of (20) or (23), wherein the reporter gene is luciferase, chloramphenicol acetyltransferase, green fluorescent protein, or β-galactosidase;

(25) the method of any one of (18) to (24), wherein an inflammatory stimulus is given to cells and wherein the biological activity transduced through TAK1 or through TAK1 and TAB1 is detected and/or measured;

(26) the method of (25), wherein the inflammatory stimulus is IL-1, TNF, or LPS;

(27) the method of any one of (1) to (26), wherein the inflammatory cytokine is IL-1, TNF, IL-10, or IL-6;

(28) a compound for inhibiting signal transduction through inflammatory cytokines, the compound that can be isolated by the method of any one of (1) to (27);

(29) a pharmaceutical composition comprising as an active ingredient the compound of (28);

(30) an inhibitor of the signal transduction through inflammatory cytokines, the inhibitor having an activity of inhibiting signal transduction through TAK1;

(31) an inhibitor of the activity of inflammatory cytokines, the inhibitor having an activity of inhibiting signal transduction through TAK1;

(32) an inhibitor of the production of inflammatory cytokines, the inhibitor having an activity of inhibiting signal transduction through TAK1;

(33) a pharmaceutical composition for inhibiting signal transduction through inflammatory cytokines, the pharmaceutical composition comprising as an active ingredient a compound inhibiting signal transduction through TAK1;

(34) a pharmaceutical composition for inhibiting the activity of inflammatory cytokines, the pharmaceutical composition comprising as an active ingredient a compound inhibiting signal transduction through TAK1;

(35) a pharmaceutical composition for inhibiting the production of inflammatory cytokines, the pharmaceutical composition comprising as an active ingredient a compound inhibiting signal transduction through TAK1;

(36) the pharmaceutical composition of any one of (33) to (35) wherein the pharmaceutical composition is an anti-inflammatory agent;

(37) the pharmaceutical composition of any one of (33) to (36), wherein the compound is a compound inhibiting binding between TAK1 and TAB1;

(38) the pharmaceutical composition of any one of (33) to (36) wherein the compound is a compound inhibiting phosphorylation by TAK1;

(39) the pharmaceutical composition of any one of (33) to (38), wherein the compound is a compound that can be isolated by the method of any one of (1) to (27); and

(40) the pharmaceutical composition of any one of (33) to (39), wherein the inflammatory cytokine is IL-1, TNF, IL-10, or IL-6.

In the present invention, the term "peptide" means a compound in which amino acids are bonded to each other by peptide bond. Accordingly, the inventive peptide includes long chains of amino acids, namely, polypeptides and proteins.

In the screening of compounds based on inhibiting the binding between TAK1 and TAB1, there is no particular limitation on TAK1 used in the present invention, as far as the TAK1 has the activity of TAB1 binding. Such TAK1 includes not only the complete TAK1 having the amino acid sequence from Met at amino acid 1 to Ser at amino acid 579 in the amino acid sequence of SEQ ID NO: 2 but also a TAK1 species without the kinase activity of TAK1.

TAB1 binds to a region containing TAK1 catalytic domain having the amino acid sequence from Met at amino acid 1 to Glu at amino acid 303 shown in SEQ ID NO: 2, and thereby activating TAK1. It has been disclosed herein that TAB1 binds to the amino acid sequence from Val at amino acid 76 to Gln at amino acid 303 of TAK1 sequence shown in SEQ ID NO: 2. A TAK1 species, which has the amino acid sequence from Val at amino acid 76 to Gln at amino acid 303 of TAK1 sequence shown in SEQ ID NO: 2, does not exhibit the kinase activity, but has the activity of binding to TAB1, and thus the species can be used in the present invention.

Accordingly, TAK1 to be used in the present invention can be a TAK1 species which has the amino acid sequence from Val at amino acid 76 to Gln at amino acid 303 in SEQ ID NO: 2 and which has a amino acid sequence modified by one or more amino acid substitutions, deletions, and/or additions within the amino acid sequence from Met at amino acid 1 to Ile at amino acid 75 and within the amino acid sequence from Tyr at amino acid 304 to Ser at amino acid 579.

As far as a TAK1 species has the TAB1-binding activity, TAK1 can be the TAK1 species of which amino acid sequence is modified by one or more amino acid substitutions, deletions, and/or additions in the amino acid sequence from Val at amino acid 76 to Gln at amino acid 303 in SEQ ID NO: 2.

On the other hand, in the screening of compounds based on inhibiting TAK1 kinase activity, there is no particular limitation on TAK1 as far as the TAK1 species has the kinase activity.

TAK1 to be used includes, for example, the complete TAK1 having the amino acid sequence from Met at amino acid 1 to Ser at amino acid 579 in the amino acid sequence shown in SEQ ID NO: 2 and having the biological activity of TAK1. It has been found that the biological activities of TAK1 are the binding activity to TAB1 as well as the kinase activity to MAPKK in its activated state. Namely, TAK1 is activated upon the binding with TAB1 and then exhibits the kinase activity.

In more detail, it has been revealed that TAK1 exhibits the kinase activity (phosphorylation) in its activated state and the kinase activity is responsible for the phosphorylation of MAPKK, for example, MKK3 (Moriguchi, T. et al., J. Biol. Chem. (1996) 271, 13675-13679), MKK6 (Moriguchi, T. et al., J. Biol. Chem. (1996) 271, 13675-13679), or XMEK2/SEKI (Shibuya, H. et al., Science (1996) 272, 1179-1182); and the phosphorylation activates the kinase activity of MAPKK.

TAK1 to be used in the present invention can also be a TAK1 species having the biological activity of TAK1 and having the amino acid sequence which is modified by one or more amino acid substitutions, deletions, and/or additions in the amino acid sequence shown in SEQ ID NO: 2. More specifically, TAK1 to be used in the present invention may have the amino acid sequence shown in SEQ ID NO: 2, in which one, two or more amino acid residues, preferably 1 to 20 amino acid residues, more preferably 1 to 10 amino acid residues are substituted, as far as the TAK1 species has the biological activity of TAK1.

TAK1 to be used in the present invention may also have the amino acid sequence shown in SEQ ID NO: 2, in which one, two or more amino acid residues, preferably 1 to 276 amino acid residues, more preferably 1 to 10 amino acid residues are deleted. TAK1 to be used in the present invention may also have the amino acid sequence shown in SEQ ID NO: 2, in which one, two or more amino acid residues, preferably 1 to 30 amino acid residues, more preferably 1 to 20 amino acid residues are added.

One example of TAK1 of which amino acid sequence is modified by one or more amino acid substitutions, deletions, and/or additions in the amino acid sequence of human TAK1 shown in SEQ ID NO: 2 is a mouse-derived TAK1 in which Ser is substituted for Gly at amino acid 16, Arg is substituted for His at amino acid 372, Val is substituted for Ala at amino acid 400, Ala is substituted for Thr at amino acid 403, and Ala is substituted for Thr at amino acid 449.

It has been already known that a peptide having an amino acid sequence that is modified by one or more amino acid substitutions, deletions, and/or additions in a amino acid sequence is still capable of having its original biological activity (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G. et al., Proc. Natl. Acad. Sci. USA (1982) 79, 6409-6413).

Indeed, it has been revealed that a TAK1 species having merely the amino acid sequence from Met at amino acid 1 to Gln at amino acid 303 in SEQ ID NO: 2 is capable of exhibiting the biological activity. Thus, TAK1 to be used in the present invention can be a TAK1 species having the amino acid sequence from Met at amino acid 1 to Gln at amino acid 303 in SEQ ID NO: 2, and having the amino acid sequence which is modified by one or more amino acid substitutions, deletions, and/or additions within the amino acid sequence from Tyr at amino acid 304 to Ser at amino acid 579. TAK1 can be a TAK1 species having an amino acid sequence which is modified by one or more amino acid substitutions, deletions, and/or additions within the amino acid sequence from Met at amino acid 1 to Gln at amino acid 303 in SEQ ID NO: 2, as far as the TAK1 species has the biological activity.

Further, TAK1 lacking at least 21 amino acid residues at the amino terminal end (N terminus) still has the original biological activity, and thus such a TAK1 species can be used in the present invention.

An E. coli strain containing plasmid phTAK1, which comprises a DNA encoding a human TAK1 peptide having the amino acid sequence from Met at amino acid 1 to Ser at amino acid 579 in the TAK1 amino acid sequence shown in SEQ ID NO: 2, was named Escherichia coli JM109 (phTAK1) and has been deposited internationally under the Budapest Treaty as an accession No. FERM BP-5598 in The National Institute of Bioscience and Human-Technology, The Agency of Industrial Science and Technology (1-1-3 Higashi, Tsukuba, Ibaraki, Japan) on Jul. 19, 1996.

In the screening of compounds based on inhibiting the binding between TAK1 and TAB1, there is no particular limitation on TAB1 to be used in the present invention as far as the TAB1 species has the TAK1-binding activity. The TAB1 species may lack in the biological activity of TAB1.

TAB1 to be used in the present invention can be a TAB1 species having an amino acid sequence which is modified by one or more amino acid substitutions, deletions, and/or additions in the amino acid sequence from Met at amino acid 1 to Pro at amino acid 504 in SEQ ID NO: 4, as far as the TAB1 species has the TAK1-binding activity.

On the other hand, in the screening of compounds based on inhibiting the kinase activity of TAK1, there is no particular limitation on TAB1 as far as the TAB1 species has the activity of activating the kinase activity of TAK1.

TAB1 to be used includes the complete TAB1 having the amino acid sequence from Met at amino acid 1 to Pro at amino acid 504 shown in SEQ ID NO: 4, and having the biological activity of TAB1. It has been found that the biological activity of TAB1 is the activity of activating TAK1 by binding to the TAK1.

In more detail, it has been revealed that the biological activity of TAB1 is the activity of activating the kinase activity of TAK1 to MAPKK by the binding of TAB1 to a region containing TAK1 catalytic domain comprising the amino acid sequence from Met at amino acid 1 to Glu at amino acid 303 of TAK1.

TAB1 to be used can be a TAB1 species having the biological activity of TAB1, and having an amino acid sequence modified by one or more amino acid substitutions, deletions, and/or additions in the amino acid sequence shown in SEQ ID NO: 4. More specifically, TAB1 used in the present invention can be a TAB1 species having 1, 2 or more amino acid substitutions, preferably 1 to 20 amino acid substitutions, more preferably 1 to 10 amino acid substitutions in the amino acid shown in SEQ ID NO: 4, as far as the TAB1 species has the biological activity of TAB1.

TAB1 to be used may also have the amino acid sequence shown in SEQ ID NO: 4, in which one, two or more amino acid residues, preferably 1 to 436 amino acid residues, more preferably 1 to 10 amino acid residues are deleted. TAB1 to be used may also have the amino acid sequence shown in SEQ ID NO: 4, in which one, two or more amino acid residues, preferably 1 to 30 amino acid residues, more preferably 1 to 20 amino acid residues are added. TAB1 used in the present invention may also have the amino acid which is modified by the above-mentioned substitutions, deletions, and/or additions in combination.

It has been revealed that a TAB1 species having merely the amino acid sequence from Gln at amino acid 437 to Pro at amino acid 504 in SEQ ID NO: 4 is capable of exhibiting the biological activity. Thus, TAB1 used in the present invention can be a TAB1 species having the amino acid sequence from Gln at amino acid 437 to Pro at amino acid 504 in SEQ ID NO: 4, and having the amino acid sequence which is modified by one or more amino acid substitutions, deletions, and/or auditions within the amino acid sequence from Met at amino acid 4 to Asn at amino acid 436.

TAB1 can also be a TAB1 species having an amino acid sequence which is modified by one or more amino acid substitutions, deletions, and/or additions in the amino acid sequence from Gln at amino acid 437 to Pro at amino acid 504 in SEQ ID NO: 4, as far as the TAB1 species has the biological activity of TAB1.

One example of TAB1 of which amino acid sequence is modified by one or more amino acid substitutions, deletions, and/or additions in the amino acid sequence of SEQ ID NO: 4 is a TAB1 species having the amino acid sequence in which Arg is substituted for Ser at amino acid 52 or having the amino acid sequence from Gln at amino acid 437 to Pro at amino acid 504.

An *E. coli* strain containing plasmid TABI-f-4, which comprises a DNA encoding a human TAB1 peptide having the amino acid sequence from Met at amino acid 1 to Pro at amino acid 504 in the TAB1 amino acid sequence shown in SEQ ID NO: 4, was named *Escherichia coli* DH5α (TABI-f-4) and has been deposited internationally under the Budapest Treaty as an accession No. FERM BP-5599 in The National Institute of Bioscience and Human-Technology, The Agency of Industrial Science and Technology (1-1-3 Higashi, Tsukuba, Ibaraki, Japan) on Jul. 19, 1996.

An *E. coli* strain containing plasmid pBS-TAB1, which comprises a DNA encoding the above-mentioned human TAB1 peptide having the amino acid sequence from Met at amino acid 1 to Pro at amino acid 504 in the TAB1 amino acid sequence shown in SEQ ID NO: 4 where Arg has been substituted for Ser at amino acid 52, was named *Escherichia coli* HB101 (pBS-TAB1) and has been deposited internationally under the Budapest Treaty as an accession No. FERM BP-5508 in The National Institute of Bioscience and Human-Technology, The Agency of Industrial Science and Technology (1-1-3 Higashi, Tsukuba, Ibaraki, Japan) on Apr. 19, 1996.

There can be various molecular species of TAK1 and/or TAB1 to be used in the present invention, which are different in amino acid sequence, molecule weight, isoelectric point, the presence or absence and position of glycosylation, sugar chain structure, phosphorylation state, and/or the presence or absence of disulfide bond, depending on the origin, host producing them, and/or the type of purification method. However, human-derived TAK1 and/or TAB1 are preferable while the proteins may have any structures, as far as the proteins can be suitably used in the present invention.

The above-mentioned proteins used in the present invention can be fusion peptides of the above-mentioned proteins and other peptides. The fusion peptides can be prepared by already-known methods. The other peptides to be used for the fusion with the above-mentioned proteins can be any peptides as far as the peptides are effectively used in the present invention.

The peptide is exemplified by FLAG (Hopp, T. P. et al., BioTechnology (1988) 6, 1204-1210), 6×His of six histidine (His) residues, 10×His, influenza hemagglutinin (HA), human c-myc fragment, a fragment of VSV-GP, a fragment of p18HIV, T7-tag, HSV-tag, E-tag, a fragment of SV40 T antigen, lck tag, a fragment of α-tubulin, B-tag, a fragment of Protein C, and the like. Such already-known peptides are used. Other examples of the peptide include glutathione-S-transferase (GST), influenza hemagglutinin (HA), immunoglobulin constant region, β-galactosidase, maltose-binding protein (MBP), etc. Commercially available ones can be used.

The above-mentioned proteins to be used in the present invention can be the proteins encoded by DNAs encoding proteins having the biological activities and capable of hybridizing to the DNA encoding the above-mentioned proteins.

DNA encoding TAK1 to be used in the present invention is exemplified by a DNA having the nucleotide sequence from A at nucleotide 183 to A at nucleotide 1919 in SEQ ID NO: 1. DNA encoding TAB1 to be used in the present invention is exemplified by a DNA having the nucleotide sequence from A at nucleotide 30 to G at nucleotide 1541 in SEQ ID NO: 3.

Each of DNAs encoding the proteins to be used in the present invention can be a DNA capable of hybridizing to the nucleotide sequence of SEQ ID NO: 1 or 3 and encoding a protein having the biological activity. Hybridization condition for the DNA encoding the protein to be used in the present invention may be the conditions with suitable stringency.

Such a hybridization condition can be, for example, the condition with low stringency. The condition with low stringency is, for example, a washing condition of 42° C., 5×SSC, 0.1% sodium dodecyl sulfate, and 50% formamide. The conditions with high stringency are more preferable. The condition with high stringency is, for example, a washing condition of 60° C., 0.1×SSC, and 0.1% sodium dodecyl sulfate. It has been already known that a protein encoded by a DNA capable of hybridizing to a nucleotide sequence encoding a certain protein under a condition with suitable stringency shares the same biological activity with the latter protein.

DNA encoding TAK1 or TAB1 to be used in the present invention can be a DNA of any origin, as far as the DNA contains the nucleotide sequence of SEQ ID NO: 1 or 3, respectively. Such DNAs include, for example, genomic DNA, cDNA, and synthetic DNA. These DNAs may originate from a variety of cells, tissue, or organ, or cDNA library or genomic library derived from any species in addition to human. The libraries may be commercially available DNA libraries. The vector used for the libraries can be any vector including plasmid, bacteriophage, and YAC vectors.

As described below, TAK1 or TAB1 to be used in the present invention can be obtained as a recombinant protein produced by the use of gene recombination techniques using DNAs encoding these proteins. For example, the nucleotide sequence of a gene encoding each protein described herein can be cloned from cell, tissue, or organ expressing the protein, and then inserted into an appropriate vector, and the resulting DNA construct is introduced into a host to produce the recombinant protein. Such recombinant proteins can be also usable in the present invention.

Specifically, mRNA of the gene encoding the protein to be used in the present invention is isolated from cell, tissue, or organ expressing the protein. The mRNA is isolated from total RNA prepared by a known method, for example, guanidine-ultracentrifugation method (Chirgwin, J. M. et al., Biochemistry (1979) 18, 5294-5299) and AGPC method (Chomczynski, P. and Sacchi, N., Anal. Biochem. (1987) 162, 156-159) and purified by using an mRNA Purification Kit (Pharmacia) and such. Alternatively, the mRNA can be directly prepared by using a QuickPrep mRNA Purification Kit (Pharmacia).

Messenger RNA obtained is used for synthesizing cDNA corresponding to the gene by using reverse transcriptase. The cDNA synthesis can be performed by using an AMV Reverse Transcriptase First-strand cDNA Synthesis Kit (Seikagaku Co.) or the like. Synthesis and amplification of cDNA can be carried out by using Marathon cDNA Amplification kit (CLONTECH) and 5'-RACE (Frohman, M. A. et al., Proc. Natl. Acad. Sci. U.S.A. (1988) 85, 8998-9002; Belyavsky, A. et al., Nucleic Acids Res. (1989) 17, 2919-2932) using polymerase chain reaction (PCR).

DNA fragment of interest is prepared from the PCR products obtained, and then ligated with a vector DNA to give a recombinant vector. The ligated DNA is then introduced into E. coli or the like, and resulting colonies are selected to prepare a desired recombinant vector. Nucleotide sequence of the target DNA is verified by a known method, for example, dideoxy nucleotide chain termination method. If the DNA of interest is obtained, it is integrated into an expression vector.

DNA encoding the protein to be used in the present invention may originate from a variety of cells, tissue, or organ, or cDNA library or genomic library obtained from any species in addition to human. The libraries may be commercially available DNA libraries. The vector used for the libraries can be any vector including plasmid, bacteriophage, and YAC vectors.

DNA encoding the protein to be used in the present invention can be constructed from the above-mentioned DNAs by a known method and by using commercially available kits. For example, such DNA manipulation includes the digestion by restriction enzyme, linker ligation, and insertion of initiation codon (ATG) and/or termination codon (TAA, TGA, or TAG).

Expression vector for expressing the protein to be used in the present invention can be any type of vector, as far as the expression vector is used suitably in the present invention. Such expression vectors include, for example, mammal-derived expression vector (for example, pEF and pCDM8), insect cell-derived expression vector (for example, pBacPAK8), plant-derived expression vector (for example, pMH1 and pMH2), animal virus-derived expression vector (for example, pHSV and pMV), yeast-derived expression vector (for example, pNV11), Bacillus subtilis-derived expression vector (for example, pPL608 and pKTH50), and E. coli-derived expression vector (for example, pGEX, pGEMEX, and pMALp2).

The protein to be used in the present invention can be produced, for example, by connecting a DNA encoding the protein downstream of a promoter in the expression vector. The promoter/enhancer includes, for example, mammal-derived promoter/enhancer (for example, EF1-α promoter/enhancer and γ-actin promoter/enhancer), insect virus-derived promoter/enhancer (for example, polyhedrosis virus promoter/enhancer), plant-derived promoter/enhancer (for example, tobacco mosaic virus promoter/enhancer), animal virus-derived promoter/enhancer (for example, SV40 promoter/enhancer and human CMV promoter/enhancer), yeast-derived promoter/enhancer (for example, alcohol dehydrogenase promoter/enhancer), and E. coli-derived promoter/enhancer (for example, Lac promoter/enhancer, Trp promoter/enhancer, and Tac promoter/enhancer).

For example, the SV40 promoter/enhancer can be readily utilized according to the method of Mulligan et al. (Nature (1979) 277, 108). The HEF1α promoter/enhancer can be readily used according to the method of Mizushima et al. (Nucleic Acids Res. (1990) 18, 5322).

A commonly used useful promoter, a secretory signal sequence, and a gene to be expressed are functionally connected together, for the expression in E. coli. For example, the promoter includes lacZ promoter and araB promoter. LacZ promoter can be used according to the method of Ward et al. (Nature (1989) 341, 544-546; FASEB J. (1992) 6, 2422-2427), or araB promoter according to the method of Better et al. (Science (1988) 240, 1041-1043).

When TAK1 or TAB1 to be used in the present invention is expressed in a host, a signal sequence suitable for the host can be added. Such a signal sequence includes, for example, a signal sequence of a secretory protein. The signal sequence of secretory protein is exemplified by a signal sequence of mammal-derived secretory protein, for example, the signal sequence of immunoglobulin. Further, the signal sequence of secretory protein is exemplified by signal sequences of E. coli-derived secretory proteins, for example, periplasm secretory signal sequences such as OmpA and pelB (Lei, S. P. et al J. Bacteriol. (1987) 169, 4379).

The expression vector thus prepared can be introduced into a host by a known method. The method for the introduction into host is exemplified by electroporation (EMBO J. (1982) 1, 841-845) calcium-phosphate method (Virology (1973) 52, 456-467), and liposome method.

The replication origin to be used can be derived from SV40, polyoma virus, adenovirus, bovine papilloma virus (BPV), etc. Also, for the amplification of gene copies in a host cell system, the expression vector can contain as a selection marker aminoglycoside transferase (APH) gene, thymidine kinase (TK) gene, E. coli xanthine guanine phosphoribosyl transferase (HPRT) gene, dihydrofolate reductase (DHFR) gene, and the like. Further, a sequence with higher expression efficiency can be designed based on the consideration of codon usage in a host to be used for the expression (Grantham, R. et al., Nucleic Acids Research (1981) 9, p 43-p 74).

Any production system can be used for the production of the recombinant protein to be used in the present invention. The production systems that can be used for the production of recombinant proteins include in vitro and in vivo production systems. The in vitro production system includes, for example, production systems with eukaryotic cells as well as the systems with prokaryotic cells.

The production systems with eukaryotic cells are, for example, those with animal cells, plant cells, and fungus cells. Such animal cells include mammalian cells, e.g., CHO cell (J. Exp. Med. (1995) 108, 945), COS cell, myeloma cell, baby hamster kidney (BHK) cell, HeLa cell, and Vero cell; amphibian cells, e.g., Xenopus laevis oocyte (Valle, et al., Nature (1981) 291, 358-340); and insect cells, e.g., sf9, sf21, and Tn5. As CHO cell, particularly preferable to use are dhfr⁻ CHO cell, which lacks DHFRgene (Proc. Natl. Acad. Sci. USA (1980) 77, 4216-4220), and CHO K-1 cell (Proc. Natl. Acad. Sci. USA (1968) 60, 1275).

An example of plant cell is Nicotiana tabacum-derived cell. The callus culture may be used for this plant cell. Fungus cells include yeast, for example, the genus *Saccharomyces* such as *Saccharomyces cerevisiae*, and filamentous fungus, for example, the genus *Aspergillus* such as *Aspergillus niger*.

Prokaryotic cells that provide the production system are bacterial cells, including for example *E. coli* and *Bacillus subtilis*.

Those cells may be transformed with DNA of interest, and the resulting transformed cells are cultured in vitro to produce the recombinant protein. The cell culture can be performed according to a known method. For example, culture media to be utilized include DMEM, MEM, RPMI1640, and IMDM. These media may be used alone or in combination with serum supplement such as fetal calf serum (FCS) for the culture. The pH of the culture is preferably about 6 to 8. The cells are generally cultivated at about 30 to 40° C. for about 15 to 200 hours. If necessary, the culture medium may be changed with fresh one, aerated, and/or stirred. The recombinant protein is produced in the cells, in which the gene has been introduced, and recovered from the cells.

The in vivo production system is exemplified by the production system with animal or with plant. A DNA of interest is introduced into an animal or plant, and the animal or plant produces the recombinant protein in its body. Then the protein is recovered from the body.

Animals for the production system can be a mammal or insect. The mammals include goat, pig, sheep, mouse, and cow (Vicki Glaser, SPECTRUM Biotechnology Applications, 1993) In the case of mammal, a transgenic animal can also be used.

For example, in order to create a fusion gene for the preparation of the recombinant protein, a DNA of interest is inserted into a gene encoding a protein, such as goat β-casein, inherently produced into milk. A DNA fragment comprising the fusion gene, in which the DNA of interest is inserted, is injected into a goat embryo, and the embryo is introduced into a female goat. The recipient goat may give birth to transgenic babies. The created transgenic individuals or the progenies thereof may give milk, and the desired recombinant protein can be obtained from the milk. In order to increase the secretion of milk containing the recombinant protein produced in the transgenic goat, an adequate hormonal treatment of the transgenic goat can be utilized (Ebert, K. M. et al., Bio/Technology (1994) 12, 699-702).

An insect that can be used for the production system is, for example, silk worm. In this case, baculovirus containing a DNA of interest is infected into a silk worm, and the desired recombinant protein can be obtained from the body fluid of the silk worm (Maeda, S. et al., Nature (1985) 315, 592-594).

Further, a plant for the production system can be, for example, tobacco. In the case of tobacco, a DNA of interest is inserted into a plant expression vector, for example, pMON 530. The resulting vector is introduced into bacteria such as *Agrobacterium tumefaciens*. The bacteria are infected to tobacco, for example, *Nicotiana tabacum*. The desired recombinant protein can be obtained from the leaves of the tobacco (Julian, K.-C. Ma et al., Eur. J. Immunol. (1994) 24, 131-138).

The gene is introduced into any of these animal and plant as described above. The animal or plant produces the recombinant protein in the body thereof, then the protein is recovered from the body. The recombinant protein expressed and produced as mentioned above may be separated from intracellular or extracellular materials, or the host, and then purified into homogeneity. Separation and purification methods for protein to be used in the present invention may be commonly used ones, which are not to be restricted to any specific ones.

For example, the separation and purification of the protein can be performed by the appropriately selected and combined use of column chromatographies such as affinity chromatography, filter, ultrafiltration, salting-out, dialysis, SDS polyacrylamide gel electrophoresis, isoelectric focusing, and others (Antibodies: A Laboratory Manual. Ed Harlow and David Lane, Cold Spring Harbor Laboratory, 1988).

The chromatography includes, for example, affinity chromatography, ion-exchange chromatography, hydrophobic chromatography, gel filtration, reverse-phase chromatography, adsorption chromatography, and the like (Strategies for Protein Purification and Characterization: A Laboratory Course Manual. Ed Daniel R. Marshak et al., Cold Spring Harbor Laboratory Press, 1996). The chromatographic procedures can be carried out by liquid-phase chromatography such as HPLC, FPLC, or the like.

Protein concentration can be measured by using a known method, for example, a method with measuring absorbance or Bradford's method.

The samples to be tested by the inventive screening method include, for example, peptide, purified or crude protein, synthetic compound, materials fermented with microorganism, extract from marine organism, plant extract, prokaryotic cell extract, extract from single-cell eukaryote, or extract from animal cells, or the libraries thereof.

These test samples contain a compound that is expected to inhibit or suppress the binding between TAK1 and TAB1, a compound that is expected to inhibit or suppress the of kinase activity of TAK1 (phosphorylation), or a compound that is expected to inhibit or suppress the kinase activity of TAK1 (phosphorylation) that is generated by TAK1 and TAB1, or contain these compounds.

These compounds, which can be isolated by the inventive screening method, as described above, inhibit or suppress the TAK1 activity, or TAK1 and TAB1 activities, and thereby inhibiting or suppressing the signal transduction through inflammatory cytokines; inhibiting or suppressing the production of inflammatory cytokines; inhibiting or suppressing physiological activity of inflammatory cytokines; or inhibiting or suppressing the signal transduction by inflammatory stimulation.

In the present invention, an "inflammatory cytokine" indicates a common cytokine involved in inflammatory reaction, and specifically IL-1 (for example, IL-1α and IL-1β), TNF (for example, TNFα and TNFβ) IL-6, IL-10, IL-4, chemokine such as IL-8, MCP-1, etc.

One embodiment of the inventive screening method is conducted by contacting TAK1 and TAB1 with a test sample, then detecting the binding between TAK1 and TAB1, and selecting a compound inhibiting the binding between TAK1 and TAB1.

The screening system provided by the present invention is to be conducted as an in vitro assay system. A specific example of such in vitro assay system is a cell-free system. Specifically, TAK1 and TAB1 are used in combination, and either of them is linked to a support, the other and a test sample are added thereto and incubated. After the support is washed, the binding of the latter protein to the former linked to the support is detected or measured.

The proteins to be used in the present invention may be purified or crude proteins that are produced by cells inherently expressing the proteins, cells in which DNAs encoding the proteins are introduced, or animals or plants in which DNAs encoding the proteins are introduced.

The proteins to be used in the present invention may be linked to a support. First, either of TAK1 or TAB1, which is purified or crude, is linked to a support. The immobilization of the protein on a support may be performed by a standard method. Supports for the protein immobilization are, for example, insoluble polysaccharides such as agarose, dextran, and cellulose, synthetic resins such as polystyrene, polyacrylamide, and silicon, etc. More specifically, commercially available beads or plates, which are manufactured from them as raw materials, are used. In the case of beads, a column or the like may be used as packed with the beads. Such a plate can be a multi-well plate (96-well multi-well plate, etc.) or a biosensor chip.

The immobilization of protein on a support can be performed by a commonly used method in which chemical bonding, physical adsorption, or the like is used. Alternatively, protein can be linked to a support where an antibody specifically recognizing the protein is pre-immobilized by binding the antibody to the protein. Protein can also be immobilized via avidin/biotin.

The binding between TAK1 and TAB1 is generally allowed in a buffer. The buffer is, for example, phosphate buffer, Tris buffer, or the like. Incubation condition may be a commonly used one, for example, a condition where incubation is carried out at 4° C. to room temperature for 1 to 24 hours. Washing condition after the incubation can be any of possible condition as far as the wash does not have any negative effects on the protein binding, and for example, buffers containing detergents are usable. Such detergents include, for example, 0.05% Tween20.

In order to select a target compound, TAK1, TAB1, and a test sample are incubated under an adequate condition, and then washed to separate the specific binding from non-specific one. The degree of TAK1-TAB1 binding may be then evaluated.

In the selection of a target compound, either of TAK1 or TAB1 is linked to a support. Specifically, when TAK1 is intended to be linked to a support, TAK1 is first immobilized on a support, and then a pre-mixture of TAB1 and a test sample may be added thereto, or alternatively TAB1 may be added thereto after addition of a test sample. Alternatively, when TAB1 is intended to be immobilized on a support, likewise, a pre-mixture of TAK1 and a test sample may be added, or alternatively TAK1 may be added after addition of a test sample. TAK1, TAB1, and a test sample added in the order as described above are incubated under an adequate condition, and then the degree of TAK1-TAB1 binding can be evaluated.

Together with a testing group where test samples are contacted with the protein, a control group may be used in the inventive screening method. Such control groups can be either of a negative control group without any test samples or positive control group, or both the groups.

When the bound protein is detected or measured by the inventive method, the bound protein may be just detected or quantitatively measured. In both cases, the target compound can be detected by comparing the results obtained for a negative control group without test samples, a group containing test samples, and/or a positive control group.

The activity of the target compound can be quantitatively measured by comparing values obtained from these results. In the quantitative measurement, the values obtained for the negative control group without test samples are compared with those for the groups with test samples, to detect the target compound. As compared with that for the negative control, the value with a test sample is lower, then the test sample can be judged to contain the target compound.

Further, in the case of quantitative measurement, the sample can be quantified based on a standard curve prepared by using values for a positive control group containing known amounts of a compound that is clarified to be capable of inhibiting the binding between TAK1 and TAB1. When the protein bound is larger in quantity, then it can be estimated that the compound has only lower activity for inhibition of the protein binding. On the other hand, when the amount of protein bound is smaller, the binding-inhibitory activity of the compound to inhibit the binding of the protein is presumed to be stronger.

In the present invention, a biosensor, which is based on surface plasmon resonance phenomenon, can be used to detect or measure the binding protein. By using the biosensor based on surface plasmon resonance phenomenon, the protein-protein interaction can be observed in real time as a surface plasmon resonance signal without labeling even when the amount of protein is a trace level (for example, BIAcore, Pharmacia). Accordingly, the binding of the proteins used in the present invention can be estimated by using a biosensor such as BIAcore.

Specifically, in the combination of TAK1 and TAB1, either one is immobilized on the sensor chip, the other protein is contacted with the sensor chip, then the latter protein bound to the immobilized one is detected as a differential resonance signal.

Such an experiment can be conducted specifically as follows. Initially, a sensor chip CM5 (Biosensor) is activated, and either of TAK1 or TAB1 is immobilized on the sensor chip. More specifically, an aqueous EDC/NHS solution (200 mM EDC (N-ethyl-N'-(3-dimethylaminopropyl)carbonate hydrochloride) and 50 mM N-hydroxysuccinimide (NHS)) is used for the activation of the sensor chip, and then the sensor chip is washed with HBS buffer (10 mM HEPES pH7.4, 150 mM NaCl, 3.4 mM EDTA, 0.05% Tween20).

Subsequently, an adequate amount of a protein exhibiting the interaction is dissolved in HBS buffer, and the solution is contacted with the sensor chip for the immobilization. After the sensor chip is washed with HBS buffer, the residual active groups on the sensor chip are blocked by ethanolamine solution (1 M ethanolamine hydrochloride, pH8.5). Again, the sensor chip is washed with HBS buffer. The resulting chip is used for the binding evaluation.

In the next step, an adequate amount of the protein dissolved in HBS buffer is injected onto the sensor chip. Then, the amount of protein, which interacts to bind to the protein immobilized on the sensor chip, is observed as an increase in the resonance signal values.

Further, in the above-mentioned binding evaluation system, a test sample is injected after the injection of the protein capable of interacting the other protein. Together with the testing group where test samples are injected, a control group may be used. Such control groups can be either of a negative control group without any test samples or positive control group, or both the groups.

The protein bound can be measured quantitatively as a differential resonance signal value. In this case, the results obtained for the negative control group without test samples are compared with those for the groups with test samples and/or for the positive control group, to detect and identify the target compound.

In the present invention, either of the proteins is labeled, and the label on the protein can be utilized to detect or measure the protein binding.

For example, in the above-mentioned screening method, one protein, which is to be mixed with a test sample and to be contacted with the other protein, is pre-labeled, and then incubated in combination with the test sample. After wash, the bound protein is detected or measured based on the label on the protein. Namely, the labeled protein and the test sample are preferably contacted with the other protein linked to the support. After the incubation, the support is washed, and then the label on the bound protein is detected or measured.

The proteins to be used in the present invention can be labeled according to a common method. Labeling substances include, for example, radioisotope, enzyme, fluorescent substance, biotin/avidin, and the like. These labeling substances may be commercially available ones. Examples of radioisotope are $^{32}P$, $^{33}P$, $^{131}I$, $^{125}I$, $^{3}H$, $^{14}C$, and $^{35}S$. The enzyme includes, for example, alkaline phosphatase, horseradish peroxidase, β-galactosidase, β-glucosidase, and the like. The fluorescent substance is exemplified by fluorescein isothiocyanate (FITC), and rhodamine. All these are commercially available, and the labeling with them can be performed by a known method.

Procedures are specifically as follows. Namely, a solution containing either of the proteins is added to a plate, and the plate is allowed to stand still overnight. After wash of the plate, blocking, for example with BSA, is conducted to avoid non-specific binding of proteins. The plate is washed again, and a test sample and the labeled protein are added thereto. A negative control group without test samples and/or positive control group is contained in this experiment. All to be tested are incubated, and then the plates are washed, and finally the bound protein is detected or measured. In the step of detection or measurement, radioisotope can be detected or measured by using liquid scintillation. When the label is an enzyme, a substrate is added to the system and the detection or measurement is based on an enzymatic change of substrate, for example, coloration, which can be detected or measured in an absorbance spectrometer. Fluorescent substances may be detected or measured in a fluorophotometer. These results are compared with values obtained for the control groups to identify the target compound.

In the present invention, a primary antibody specifically recognizing either of the proteins, in the combination of TAK1 and TAB1, can be used to detect or measure the bound protein.

For example, together with a test sample, one protein is contacted and incubated with the other protein, after wash, the bound protein is detected or measured with a primary antibody specifically recognizing the protein. Namely, the protein and the test sample are preferably contacted with the other protein linked to the support. After the incubation, the support is washed, and the bound protein is detected or measured by utilizing the primary antibody specifically recognizing the bound protein. The primary antibody is preferably labeled with a labeling substance.

Such an experiment can be conducted specifically as follows. A solution containing either of the proteins is added to a plate, and the plate is allowed to stand still overnight. After wash of the plate, blocking, for example with BSA, is conducted on the plate to avoid non-specific binding of proteins. The plate is washed again, and a test sample and the other protein are added thereto. A negative control group without test samples and/or positive control group is contained in this experiment.

All to be tested are incubated, and then the plates are washed. The antibody against the protein that has been added together with the test sample is added thereto. After appropriate incubation, the plate is washed, and the protein is detected or measured with the primary antibody specifically recognizing the protein. In the step of detection or measurement, radioisotope can be detected or measured by using liquid scintillation. When the label is an enzyme, a substrate is added to the system, and the detection or measurement is based on an enzymatic change of substrate, for example, coloration, which can be detected or measured in an absorbance spectrometer. Fluorescent substances may be detected or measured in a fluorophotometer. The results obtained are compared with those for the control groups to identify the target compound.

In the present invention, a primary antibody specifically recognizing other peptides that are fused with the protein to be used in the present invention can be used to detect or measure the bound protein.

For example, in the above-mentioned screening method, together with a test sample, either one of the proteins is contacted and incubated with the other protein, after wash, the bound protein is detected or measured with a primary antibody specifically recognizing a peptide fused with the protein. Namely, the protein and the test sample are preferably contacted with the other protein linked to the support. After the incubation, the support is washed, and then the bound protein is detected or measured by the primary antibody specifically recognizing the peptide fused with the bound protein. The primary antibody is preferably labeled with a labeling substance.

Such an experiment can be conducted specifically as follows. Namely, a solution containing either of the proteins is added to a plate, and the plate is allowed to stand still overnight. After wash of the plate, blocking, for example with BSA, is conducted on the plate to avoid non-specific binding of proteins. The plate is washed again, and a test sample and the other protein fused with a peptide are added thereto. A negative control group without test samples and/or positive control is contained in this experiment.

All to be tested are incubated, and then the plates are washed. The antibody against the peptide fused with the protein that has been added together with the test sample is added thereto. After suitable incubation, the plate is washed, and the protein is detected or measured with the primary antibody specifically recognizing the peptide fused with the protein. In the step of detection or measurement, radioisotope can be detected or measured by using liquid scintillation. When the label is an enzyme, a substrate is added to the system, and the detection or measurement is based on an enzymatic change of substrate, for example, coloration, which can be detected or measured in an absorbance spectrometer. Fluorescent substances may be detected or measured in a fluorophotometer. The results obtained are compared with those for the control groups to identify the target compound.

In the present invention, a primary antibody specifically recognizing the protein to be used in the present invention and a secondary antibody specifically recognizing the primary antibody can be used to detect or measure the bound protein.

For example, together with a test sample, either one of the proteins is contacted and incubated with the other protein, after wash, the bound protein is detected or measured with a primary antibody specifically recognizing the protein and the secondary antibody specifically recognizing the primary antibody. Namely, the protein and the test sample are preferably contacted with the other protein linked to the support. After the incubation and wash, the bound protein is detected or measured by the primary antibody specifically recognizing the protein and the secondary antibody specifically recognizing the primary antibody. The secondary antibody is preferably labeled with a labeling substance.

Such an experiment can be conducted specifically as follows. Namely, a solution containing either of the proteins is added to a plate, and the plate is allowed to stand still overnight. After wash of the plate, blocking, for example with BSA, is conducted on the plate to avoid non-specific binding of proteins. The plate is washed again, and a test sample and the other protein are added thereto. A negative control group without test samples and/or positive control group is contained in this experiment.

All to be tested are incubated, and then the plates are washed, the primary antibody against the peptide fused with the protein that has been added together with the test sample is added thereto. After appropriate incubation, the plate is washed, and then the secondary antibody specifically recognizing the primary antibody is added thereto. After suitable incubation, the plate is washed, and the protein is detected or measured with the secondary antibody specifically recognizing the primary antibody specifically recognizing the protein. In the step of detection or measurement, radioisotope can be detected or measured by using liquid scintillation. When the label is an enzyme, a substrate is added to the system, and the detection or measurement is based on an enzymatic change of substrate, for example, coloration, which can be detected or measured in an absorbance spectrometer. Fluorescent substances may be detected or measured in a fluorophotometer. The results obtained are compared with those for the control groups to select the target compound.

In the present invention, a primary antibody specifically recognizing other peptides that are fused with the protein and a secondary antibody specifically recognizing the primary antibody can be used to detect or measure the bound protein.

For example, in the above-mentioned screening method, together with a test sample, either one of the proteins is contacted and incubated with the other protein, after wash, the bound protein is detected or measured with a primary antibody specifically recognizing a peptide fused with the protein and a secondary antibody specifically recognizing the primary antibody. Namely, the protein and the test sample are preferably contacted with the other protein linked to the support. After the incubation, the support is washed, and then the bound protein is detected or measured by the primary antibody specifically recognizing the peptide fused with the bound protein and the secondary antibody specifically recognizing the primary antibody. The secondary antibody is preferably labeled with a labeling substance.

Such an experiment can be conducted specifically as follows. Namely, a solution containing either of the proteins is added to a plate, and the plate is allowed to stand still overnight. After wash of the plate, blocking, for example with BSA, is conducted to avoid non-specific binding of proteins. The plate is washed again, and a test sample and the other protein fused with a peptide are added thereto. A negative control group without test samples and/or positive control group is contained in this experiment.

All to be tested are incubated, and then the plates are washed, the primary antibody against the peptide fused with the protein that has been added together with the test sample is added thereto. After appropriate incubation, the plate is washed, then the secondary antibody specifically recognizing the primary antibody is added thereto. After suitable incubation, the plate is washed, and the protein is detected or measured with the secondary antibody specifically recognizing the primary antibody specifically recognizing the peptide fused with the protein. In the step of detection or measurement, radioisotope can be detected or measured by using liquid scintillation. When the label is an enzyme, a substrate is added to the system, and the detection or measurement is based on an enzymatic change of substrate, for example, coloration, which can be detected or measured in an absorbance spectrometer. Fluorescent substances may be detected or measured in a fluorophotometer. The results obtained are compared with those for the control groups to determine the target compound.

In more detail, the present invention can be conducted particularly preferably by Enzyme-linked Immunosorbent Assay (ELISA) as follows. Specifically, TAK1 fused with a peptide, for example 6×His, is diluted with an immobilization buffer (0.1 M $NaHCO_3$, 0.02% $NaN_3$, pH9.6). Appropriate amounts of the aqueous solution of dilution are added to respective wells of a 96-well immuno-plate (Nunc) and incubated at 4° C. overnight.

Each well is washed 3 times with a washing buffer (prepared as PBS containing 0.05% Tween20), and 200 µl of PBS containing 5% BSA (SIGMA) is added thereto, and then the plate was incubated for blocking at 4° C. overnight.

Subsequently, each well is washed 3 times with the washing buffer, adequate amounts of TAB1 fused with a peptide (e.g., FLAG), which has been diluted with a dilution buffer (1% BSA and 0.5% Tween20 in PBS) and a test sample are added thereto. The resulting mixture is incubated at room temperature for 1 hour. Each well is washed 3 times with the washing buffer, and a 100-µl aliquot of mouse anti-FLAG M2 antibody (IBI), which has been diluted to 3 µg/ml with the dilution buffer, is added to each well. The plate is incubated at room temperature for 1 hour.

Each well is washed 3 times with a washing buffer, and a 100-µl aliquot of alkaline phosphatase-labeled goat anti-mouse IgG antibody (ZYMED), which has been diluted 1000 times with the dilution buffer, is added to each well. The plate is incubated at room temperature for 1 hour. Each well is washed 5 times with a washing buffer, and a 100-µl aliquot of a coloring solution (substrate buffer (50 mM $NaHCO_3$, 10 mM $MgCl_2$, pH9.8) containing 1 mg/ml p-phenylphosphate; SIGMA) is added to each well. The plate is incubated at room temperature, and then absorbance at 405 nm is measured by using a microplate reader (Model3550, BIO-RAD). The results obtained are compared with those for the negative control group and/or positive control group to identify the target compound.

In addition, protein G or protein A instead of the secondary antibody can be utilized in the detection or measurement using the antibody of the present invention.

The inventive screening method can be practiced by using High Throughput Screening (HTS). Specifically, the steps from the start to the blocking are performed manually, and the remaining reactions are automated by using a robot, thereby achieving a high-throughput screening.

Specifically, TAK1 fused with a peptide, for example 6×His, is diluted with an immobilization buffer (0.1 M $NaHCO_3$, 0.02% $NaN_3$, pH9.6). Appropriate amounts of the aqueous solution of dilution are added to respective wells of a 96-well immuno-plate (Nunc) and incubated at 4° C. overnight.

Each well is washed 3 times with a washing buffer (prepared as PBS containing 0.05% Tween20), and 200 µl of PBS containing 5% BSA (SIGMA) is added thereto, and then the plate was incubated for blocking at 4° C. overnight.

Subsequently, for example, the immuno-plate subjected to the blocking treatment is placed in a Biomek2000 HTS system (Beckman) and the device is operated by a system control program. In this process, a dispenser such as Biomek 2000 dispenser (Beckman) or Multipipette 96-well dispenser (Sagian) can be used to dispense solutions to each well or to remove them from well of the immuno-plate. Further, EL404 microplate washer (Bio Tek) can be used to wash each well of the immuno-plate. Absorbance can be measured by using a SPECTRAmax250 plate reader (Molecular Devices).

The operating program is set to conduct the following steps. Specifically, each well is washed 3 times with the washing buffer, and then adequate amounts of a test sample and TAB1 fused with a peptide, for example maltose-binding protein (MBP), which has been diluted with a dilution buffer (1% BSA and 0.5% Tween20 in PBS), are added thereto. A negative control group without test samples and a positive control are simultaneously managed. These all samples are incubated at room temperature for 1 hour.

Each well is washed 3 times with a washing buffer, and a 100-μl aliquot of rabbit anti-MBP antiserum (New England Biolabs), which has been diluted 5000 times with the dilution buffer, is added thereto. The plate is incubated at room temperature for 1 hour. Each well is washed 3 times with a washing buffer, and a 100-μl aliquot of alkaline phosphatase-labeled goat anti-rabbit IgG antibody (TAGO), which has been diluted 5000 times with the dilution buffer, is added to each well. The plate is incubated at room temperature for 1 hour.

Each well is washed 5 times with a washing buffer, and a 100-μl aliquot of a coloring solution (substrate buffer (50 mM $NaHCO_3$, 10 mM $MgCl_2$, pH9.8) containing 1 mg/ml p-nitrophenylphosphate; SIGMA) is added to each well. The plate is incubated at room temperature, and then absorbance at 405 nm is measured by using a microplate reader, Biomek-plate reader (Beckman/Molecular Devices). The results obtained are compared with those for control groups to identify the target compound.

Antibodies to be used in the present invention can be commercially available antibodies and antibodies contained in commercially available kits as well as monoclonal or polyclonal antibodies that can be prepared by using well-known methods.

Monoclonal antibody can be prepared by using a desired antigen for sensitization. Immunization is performed by using this antigen according to a commonly used method. The resulting immune-cells are fused with publicly known parental cells by a standard cell fusion method. Cells producing monoclonal antibody are screened by a standard screening method.

Specifically, monoclonal antibody or polyclonal antibody is generated as follows. For example, the origin of sensitizing antigen to obtain antibody is not restricted to a particular animal species, but it is preferred to use an antigen that is of the same mammalian origin as the peptide actually used in the present invention, for example, human, mouse, or rat. Among them, the sensitizing antigen originating from human is particularly preferable. For example, when human TAK1 or human TAB1 is intended to use as the sensitizing antigen, their nucleotide sequences and amino acid sequences can be obtained by the gene sequences disclosed herein. Alternatively, when other peptides to be fused with the above-mentioned proteins are used as the sensitizing antigens, the peptides can be prepared by chemical synthesis or genetic engineering.

The protein or peptide to be used as the sensitizing antigen may be the full-length one or the fragment thereof. The fragment includes, for example, a C-terminal fragment or N-terminal fragment.

There is no particular limitation on the mammal to be immunized with the sensitizing antigen, but it is preferable to select with considering compatibility to a parental cell to be used for cell fusion. Generally used are animals belonging to Rodentia, Lagomorpha, and Primates.

An animal of Rodentia is exemplified, for example, by mouse, rat, and hamster. Lagomorpha animal includes, for example, rabbit. An animal of Primates includes, for example, monkey. Monkeys such as those of Catarrhini (old-world monkey) including crab-eating monkey, rhesus monkey, hamadryas baboon, and chimpanzee can be used.

Animal is immunized with a sensitizing antigen according to a known method. For example, as a standard method, the sensitizing antigen is intraperitoneally or subcutaneously injected to a mammal. Specifically, the sensitizing antigen is appropriately diluted and/or suspended in Phosphate-Buffered Saline (PBS), physiological saline, etc. If necessary, the solution is mixed with an adequate amount of a standard adjuvant e.g., Freund's complete adjuvant, emulsified, and preferably given to a mammal several times at 4 to 21 day intervals. An appropriate carrier may also be used at the time of the immunization with the sensitizing antigen. After the immunization, increases in the serum level of desired antibody are confirmed by a commonly used method.

In order to obtain polyclonal antibody, after the verification of elevated serum level of desired antibody, blood is collected from the mammal sensitized with the antigen. Serum is separated from the blood by a known method. As polyclonal antibody, serum containing the polyclonal antibody may be used, or alternatively, if needed, a fraction containing the polyclonal antibody may be further isolated from the serum.

In order to obtain monoclonal antibody, after the verification of elevated serum level of desired antibody in a mammal sensitized with the above-mentioned antigen, immune-cells are collected from the mammal. The cells are subjected to the cell fusion. Preferably, the immune-cells to be utilized for the cell fusion are spleen cells in particular.

The other parental cells to be fused with the above-mentioned immune-cells include mammalian myeloma cells. Such cells used preferably may be various known cell lines.

Basically, cell fusion between the above-mentioned immune-cells and myeloma cells can be performed according to a known method including, for example, the method of Milstein et al. (Galfre, G. and Milstein, C., Methods Enzymol. (1981) 73, 3-46), etc.

More specifically, the above-mentioned cell fusion may be conducted, for example, in the presence of cell fusion-enhancing agent in a commonly used nutrient culture medium. The cell fusion-enhancing agent is, for example, polyethylene glycol (PEG), Sendai virus (HVJ), or the like. An adjuvant, such as dimethyl sulfoxide or the like, may optionally be used together to enhance the efficiency of fusion.

A mixing ratio between immune-cells and myeloma cells preferably ranges, for example, from 1:1 to 1:10 of myeloma cell vs. immune-cells. Cell culture medium for the above-mentioned cell fusion includes, for example, RPMI1640 and MEM media that are preferred for the proliferation of the myeloma cell lines, and other standard culture media that are used in this type of cell culture. Serum supplements such as fetal calf serum (FCS) can be used together.

The cell fusion is carried out as follows. The above-mentioned immune-cells are mixed well with myeloma cells at a given ratio in the above-mentioned medium. A solution of PEG (for example, averaged molecule weight of about 1000 to 6000), which has been pre-heated at about 37° C., is generally added to the cell mixture at a concentration of 30 to 60% (W/V), and mixed to form the fused cells (hybridomas) of interest. Subsequently, the agent for cell fusion and other agents, which are not preferable for the growth of hybridomas, can be removed by repeatedly conducting the following procedures: adding an appropriate culture medium to the cell mixture; centrifuging them; and removing the supernatant.

The hybridomas are selected by culturing the cells in a standard selection medium, for example, HAT medium (a medium containing hypoxanthine, aminopterin, and thymidine). The culture in the HAT medium is continued till all cells except the hybridomas of interest (non-fused cells) are sufficiently killed, generally, for several days to several weeks. Then, the commonly used limiting dilution method is employed to screen and clone the hybridomas producing antibodies of interest.

Further, in addition to the preparation of hybridomas in which an animal except human is immunized with an antigen, the following alternative method can be employed. Human lymphocytes, for example, EB virus-infected human lymphocytes are in vitro sensitized with a protein or peptide, cells expressing them, or lysate of the cells. The sensitized lymphocytes are fused with human-derived myeloma cells (e.g., U266 cell) having permanent division potential to obtain hybridomas producing desired human antibodies having the activity of binding to the peptide (Unexamined Published Japanese Patent Application No. Sho 63-17688).

Another alternative method may be employed. A transgenic animal having human antibody gene repertoire is immunized with an antigen, which may be a protein or peptide, cells expressing them, or lysate of the cells, to obtain cells producing antibody. The cells are fused with myeloma cells to prepare hybridomas, and thereby obtaining human antibodies against the protein or peptide to be used in the present invention (refer to WO92-03918, WO93-2227, WO94-02602, WO94-25585, WO96-33735, and WO96-34096).

The prepared hybridomas producing monoclonal antibody can be cultivated and passaged in a standard culture medium, and also can be stored in liquid nitrogen over the long term.

Monoclonal antibodies can be prepared from the hybridomas by the following methods and such. The hybridomas are cultured according to a standard procedure, and the monoclonal antibody can be obtained as the culture supernatant. Alternatively, the hybridomas are transplanted and grown in a mammal that has the compatibility to the hybridomas, and the monoclonal antibody can be obtained as the ascites. The former method is suitable for the preparation of highly pure antibody, and the latter is suitable for the preparation of antibody in large quantity.

In addition to the antibody production by hybridoma, oncogene-immortalized immune-cells such as sensitized lymphocytes producing antibody of interest can be used for this purpose.

The monoclonal antibody thus obtained can also be prepared as a recombinant antibody produced by utilizing gene recombination techniques. For example, the recombinant antibody can be produced by cloning the antibody gene from the immune-cells such as hybridomas or antibody-producing sensitized lymphocytes, inserting the gene into an appropriate vector, and introducing the vector into a host. In the present invention, the recombinant antibody can be used (refer to, for example, Borrebaeck, C. A. K. and Larrick, J. W., THERAPEUTIC MONOCLONAL ANTIBODIES, Published in the United Kingdom by MACMILLAN PUBLISHERS LTD, 1990).

The antibody to be used in the present invention may be an antibody fragment thereof or modified antibody, as far as it has the desired binding activity. For example, such an antibody fragment includes Fab, F(ab')2, Fv, or single chain Fv (scFv) in which Fv of H chain and Fv of L chain are linked to each other with an appropriate linker. Specifically, an antibody is treated with an enzyme, for example, papain or pepsin, to provide an antibody fragment. Alternatively, genes encoding the antibody fragments are constructed and inserted into an expression vector, and the resulting construct is expressed in an appropriate host cell.

The antibody expressed and produced as described above can be separated from intracellular and/or extracellular material or the hosts and then purified to homogeneity. There is no particular limitation on the method of separation and purification of the antibody used for the present invention, and any separation-purification methods for usual proteins are usable.

For example, the antibody can be separated and/or purified by the appropriately selected and combined use of column chromatographies such as affinity chromatography and the like, filter, ultrafiltration, salting-out, dialysis, SDS polyacrylamide gel electrophoresis, isoelectric focusing, and others (Antibodies: A Laboratory Manual. Ed Harlow and David Lane, Cold Spring Harbor Laboratory, 1988).

A column used in affinity chromatography is exemplified by protein A column or protein G column. For example, protein A column includes Hyper D, POROS, and Sepharose F.F. (Pharmacia).

In addition to affinity chromatography, the chromatographic method includes, for example, ion-exchange chromatography, hydrophobic chromatography, gel filtration, reverse-phase chromatography, adsorption chromatography, and the like (Strategies for Protein Purification and Characterization: A Laboratory Course Manual. Ed Daniel R. Marshak et al., Cold Spring Harbor Laboratory Press, 1996). The chromatographic procedures can be carried out by liquid-phase chromatography such as HPLC, FPLC, or the like.

The concentration or activity of the antibody obtained above can be measured by a known method, for example, ELISA, enzymatic immunoassay (EIA), radioimmunoassay (RIA), or immunofluorescence.

The primary antibody or secondary antibody obtained above can be labeled according to a commonly-known method. Labeling substances include, for example, radioisotope, enzyme, fluorescent substance, and the like. These labeling substances may be commercially available ones. Examples of radioisotope are $^{32}P$, $^{33}P$, $^{131}I$, $^{125}I$, $^{3}H$, $^{14}C$, and $^{35}S$. The enzyme includes, for example, alkaline phosphatase, horseradish peroxidase, β-galactosidase, β-glucosidase, and the like. The fluorescent substance is exemplified by fluorescein isothiocyanate (FITC) and rhodamine. The labeling can be performed by a known method by obtaining these commercially available labeling substances.

The binding between TAK1 and TAB1 can also be detected and/or measured by observing change in the expression level of a reporter gene which is activated in response to the binding of the proteins. Luciferase, β-galactosidase, HIS3 gene, chloramphenicol acetyltransferase (CAT), green fluorescent protein (GFP) gene, or the like can be used as the reporter gene which is activated in response to the biological activity produced by the binding between TAK1 and TAB1.

TAK1 and TAB1 expressed in cells may be fused proteins with other peptides. The peptides to be fused with the proteins can be any peptides as far as the peptides are usable in the inventive screening method, but are preferably transcriptional regulatory factors.

For example, TAK1 and TAB1 DNAs are respectively fused with DNAs encoding respective subunits of heterodimeric transcriptional regulatory factor that is known to bind to a DNA and thereby activating the transcription of a certain reporter gene, The fusion genes are inserted into expression vectors, and the resulting DNA constructs are introduced into cells. When a test sample does not contain any compound inhibiting the binding between TAK1 and TAB1, the respective subunits fused with TAK1 and TAB1 form the heterodimer. The heterodimeric transcriptional regulatory factor binds to the DNA and thereby activating the reporter gene.

When a test sample contains a compound inhibiting the binding between TAK1 and TAB1, the compound inhibits the binding between TAK1 and TAB1. As a result, the subunits of the transcriptional regulatory factor cannot form the heterodimer, and thus the transcription of the reporter gene is not induced. The target compound can be detected or measured by observing change in the expression level of a reporter gene. The two-hybrid system (Fields, S., and Sternglanz, R., Trends. Genet. (1994) 10, 286-292) can be used when change in the expression level of a reporter gene is intended to be assayed in such a system.

The two-hybrid system may be constructed by using a commonly used method or by utilizing a commercially available kit. Examples of the commercially available two-hybrid system kit are MATCHMAKER Two-Hybrid System, Mammalian MATCHMAKER Two-Hybrid Assay Kit (both are products from CLONTECH), and HybriZAP Two-Hybrid Vector System (Stratagene).

Specifically, the following procedure is employed for the experiments. The gene encoding TAK1 is ligated with the gene encoding LexA DNA-binding domain to provide an expression vector. For example, the gene encoding full-length TAK1 of SEQ ID NO: 2 or its segment having amino acids 1 to 418 is inserted in frame into an expression plasmid pBTM116 (Vojtek, A. B., et al., Cell (1993) 74, 205-214) for the yeast two-hybrid system to construct an expression plasmid.

Next, the gene encoding full-length TAB1 of SEQ ID NO: 4 or its segment containing amino acids 1 to 504 is ligated with the gene encoding GAL4-transcription activation domain to prepare an expression vector. The expression vector can be constructed, for example, by inserting the TAB1-encoding gene in frame into an expression plasmid pGAD10 (CLONTECH) for the yeast two-hybrid system.

Each of the two-hybrid expression plasmids is transformed into cells of yeast L40 strain containing the HIS3 gene of which transcription is regulated by a promoter with a LexA-binding motif. When the cells are incubated on synthetic medium without histidine, the presence of the protein interaction results in yeast growth. Thus, the degree of transformant growth indicates increases in the expression level of the reporter gene, and the target compound can be screened.

In another embodiment of the screening system provided by the present invention, TAK1 kinase activity generated by TAK1, or by TAK1 and TAB1 is used as an index.

An in vitro kinase assay system using TAK1, or using TAK1 and TAB1 is utilized to conduct the screening where TAK1 kinase activity is used as an index. A TAK1 molecule lacking the N-terminal 22 amino acid residues constitutively shows the kinase activity. Thus, the TAK1 molecule lacking the N-terminal 22 amino acid residues is expressed in animal cells such as COS cell, bacterial cells such as E. coli, yeast cells, and so on, and then a test sample is added and incubated with TAK1. Subsequently, a substrate protein for TAK1, such as MKK6, together with $^{32}$P-ATP, is added to TAK1 separated with an anti-TAK1 antibody or the like to perform kinase reaction. The activity is then detected or measured. After the kinase reaction, the amount of $^{32}$P-ATP incorporated into the substrate protein by the phosphorylation thereof is assayed to evaluate the TAK1 kinase activity. The result is compared to that of a negative control without any test sample to identify a compound directly inhibiting TAK1 kinase activity.

Such an in vitro kinase assay system using TAK1 and TAB1 is exemplified by the one as described in a reference (Moriguchi, T., et al. J. Biol. Chem. 271: 13675-13679 (1996)). For example, TAK1 and TAB1 expressed in animal cells such as COS cell, E. coli, yeast, and such are incubated with a test sample in vitro, and a substrate protein, such as MKK6, together with $^{32}$P-ATP, is added to TAK1 separated with an anti-TAK1 antibody or the like to perform kinase reaction. The activity is then detected or measured. After the kinase reaction, the amount of $^{32}$P-ATP incorporated into the substrate protein by the phosphorylation thereof is assayed to evaluate the TAK1 kinase activity. The result is compared to that of a negative control without any test sample to identify a compound inhibiting TAK1 kinase activity.

The screening method using TAK1 kinase activity as an index can be used for High Throughput Screening (HTS). Specifically, the steps of addition, mixing, and respective reactions for each sample are automated by using a robot, the phosphorylation degree of substrate protein is detected by scintillation proximity assay method (Bothworth, N. and Towers, P., Nature, 341: 167-168, 1989), and thereby achieving a high-throughput screening.

Specifically, together with a test sample, TAK1 and TAB1 expressed in animal cells such as COS cell, E. coli, or yeast, are added to each well of 96-well microplate, and the plate is incubated. Subsequently, $^{32}$P-ATP and a substrate protein (e.g., MKK6) are added to the above-mentioned reaction solutions for the kinase reaction. In the next step, an anti-MKK6 antibody is added to each well, and then SPA beads (Amersham) which are coated by protein A or an antibody specifically recognizing other antibodies in a species-specific manner are added to each well. After incubation, radioactivity incorporated into the substrate protein is measured by using a MicroBeta scintillation counter (Wallac). Alternatively, when biotinylated substrate protein is used, streptavidin-coated SPA beads can be used for the assay. The result obtained by these methods is compared to that of a control group to identify a test sample containing a compound inhibiting TAK1 kinase activity.

In yet another embodiment of the screening system provided by the present invention, the assay is performed by using cells in vitro. Specifically, a test sample is introduced into and/or contacted with cells expressing TAK1 and TAB1, and then TAK1- and TAB1-mediated transduction of biological activity is detected and/or measured. A compound reducing the biological activity is selected to obtain the target compound.

In the above-described method, proteins to be used are expressed in cells used for the assay. Examples described later have revealed that the inhibition of binding between TAK1 and TAB1 inhibits the signal transduction through inflammatory cytokines, which further inhibits the production of other inflammatory cytokines involved in the cytokine network. Accordingly, the detection and/or measurement of the TAK1-, or TAK1- and TAB1-mediated transduction of biological activity makes it possible to inhibit or suppress the signal transduction through inflammatory cytokine of interest, and based on the inhibition or suppression, makes it possible to inhibit or suppress the production of the inflammatory cytokine, to inhibit or suppress physiological activity of the inflammatory cytokine, or possible to screen a compound inhibiting or suppressing the inflammatory stimulation-induced signal transduction.

Cells expressing TAK1, or TAK1 and TAB1 can be preferably prepared by gene engineering techniques, by introducing the herein-described DNAs encoding them into cells that naturally express none of them.

Any cells can be used as cells expressing TAK1, or TAK1 and TAB1 as far as the cells can be used for the present invention. Cells usable for the present invention include prokaryotic and eukaryotic cells. The prokaryotic cells include bacterial cells, and eukaryotic cells include mammalian cells, insect cells, and yeast cells.

The genes encoding the proteins to be used in the present invention are introduced into these cell lines, and a test sample is added thereto. Then, actions reflecting the signal transduction through inflammatory cytokines, production of inflammatory cytokines, physiological activity of inflammatory cytokines, inflammatory stimulation-induced signal transduction, and so on are detected or measured. The introduction and contact of a test sample may be achieved by adding the test sample into a cell culture medium.

Biological activities transduced through the mediation of TAK1, or TAK1 and TAB1 include, for example, biological activities of inflammatory cytokines, the activity of inducing inflammatory mediators, and change in the expression levels of reporter genes.

Specific examples of inflammatory cytokine are IL-1 (e.g., IL-1α and IL-1β), TNF (e.g., TNFα and TNFβ), IL-6, etc. The biological activity of IL-1 includes the enhancement of antibody production, activation of T and/or B cells, induction of production of other cytokines including IL-6, IL-2, and IFN-δ based on cytokine network, induction of acute-phase proteins, fever, activation of vascular endothelial cells, infiltration of leukocytes, and production of collagenase and/or collagen. Accordingly, any of these actions can be detected or measured to detect the biological activity of IL-1 as an inflammatory cytokine.

The biological activity of TNF includes the activation of T cell and macrophage, induction of production of other cytokines including IL-1, IL-6, and IL-8 based on cytokine network, induction of apoptosis, production of collagenase and/or collagen, and production of prostaglandins. Accordingly, any of these actions can be detected or measured to detect the biological activity of TNF as an inflammatory cytokine. The biological activity of IL-6 includes the induction of acute-phase proteins, enhancement of antibody production, increase in hematopoietic stem cell, enhancement of neuronal cell differentiation. Accordingly, any of these actions can be detected or measured to detect the biological activity of IL-6 as an inflammatory cytokine.

Cell lines and such that are already known to show these actions can be used in the detection or measurement of these actions in order to detect the biological activity of inflammatory cytokines. For example, the activity of inducing cytokine production can be detected or measured quantitatively by assaying the amount of cytokine produced in a T cell line by ELISA or PCR.

In order to detect and/or measure the activity of inducing inflammatory mediators such as prostaglandins, as a biological activity mediated by TAK1, or TAK1 and TAB1, quantitative assay can be performed by using a macrophage cell line and a commercially available kit, etc. When the enhancement of antibody production is intended to be detected or measured, the production amount of antibody can be assayed by using a B cell line by ELISA. In the case of detection or measurement of the action of T cell activation, the evaluation can be done, for example, by analyzing cell surface markers on a T cell line by FACS or the like.

The biological activity mediated by TAK1, or TAK1 and TAB1 can be detected and/or measured by observing change in the expression level of a reporter gene which is activated in response to the biological activity. Luciferase, β-galactosidase, HIS3 gene, chloramphenicol acetyltransferase (CAT), green fluorescent protein (GFP) gene, or the like can be used as the reporter gene which is activated in response to the biological activity produced by the binding between TAK1 and TAB1. When a reporter gene is used, Northern analysis can be conducted to detect and/or measure the expression level of the gene.

The expression of inflammatory cytokines such as IL-6 and IL-1 is increased upon inflammatory stimuli such as IL-1 or LPS in monocyte/macrophage cells. Thus, in the case of detection and/or measurement of the biological activity the transduction of which is mediated by TAK1, or TAK1 and TAB1, TAK1 and/or TAB1 are expressed in the cells, an inflammatory stimulus such as IL-1 or LPS is given to the cells, thereby evaluating the signal transduction through inflammatory cytokines and the associated production of the inflammatory cytokines, physiological activity of inflammatory cytokines, the signal transduction through inflammatory stimulation, and/or the expression of inflammatory cytokines.

The term "inflammatory stimulus" means herein an stimulus inducing inflammatory reaction, including bacterial infection or injury that is a cause of disorders in living tissues, physical stimulation such as heat, coldness, radiation, or electrostimulation, chemical substance, or abnormality of biological immunity. The inflammatory stimuli include, for example, IL-1 and LPS.

Expression vectors for expressing desired proteins can be constructed by inserting genes encoding them into suitable restriction enzyme sites of expression vectors. For example, a reporter gene construct containing the luciferase gene which is regulated by an NF-κB response element derived from the IFN-β gene (p55IgkLuc; Fujita, T., et al., Gene, Dev., (1993) 7, 1354-1363) is introduced into 293 cells in which the respective expression plasmids are introduced and also into the control cells in which an expression vector without gene insert has been introduced. The respective cells are cultured in medium with or without 10 ng/ml IL-1. Luciferase activity is then assayed in the cell extracts.

When no test sample is added to the cells, the addition of IL-1 increases the luciferase activity. On the other hand, in the presence of a test sample, the luciferase activity is not increased in the cells. In other words, a target compound in the test sample inhibits the IL-1-induced elevation of reporter gene expression. Thus, increases in expression level of the reporter gene can be measured, and thereby successfully screening the target compound.

The present invention relates to an inhibitor of the signal transduction through inflammatory cytokines, inhibitor of the production of inflammatory cytokines, and an anti-inflammatory agent, which contain as an active ingredient a compound inhibiting the signal transduction through TAK1. The present invention further provides an inhibitor of the physiological activity of inflammatory cytokines and inhibitor of the signal transduction through inflammatory stimulation, which contain as an active ingredient a compound inhibiting the signal transduction through TAK1.

The term "a compound inhibiting the signal transduction through TAK1" means a compound inhibiting the biological activity of TAK1 as described herein. Such a compound inhibiting the signal transduction through TAK1 includes, for example, a compound inhibiting the binding between TAK1 and TAB1, a compound inhibiting the kinase activity of TAK1, and a compound inhibiting antagonism of substrate for TAK1.

The term "a compound inhibiting the binding between TAK1 and TAB1" indicates a compound inhibiting the interaction between TAK1 and TAB1. Such a compound inhibiting the binding between TAK1 and TAB1 includes, for example, a compound that specifically binds to TAK1 or a compound that specifically binds to TAB1. These compounds may be compounds that specifically bind to the respective targets, compete for the targets with the proteins which bind to the targets, and the competitive binding keeps the proteins which bind to the targets free from the targets. These compounds may be compounds that specifically bind to the region where TAK1 and TAB1 bind to each other and thereby inhibiting the binding between TAK1 and TAB1.

The compounds inhibiting the binding between TAK1 and TAB1 may be compounds that specifically bind to TAK1 or TAB1 and, for example, have the ability of binding to the target but lack in the ability of activation of TAK1 and/or TAB1. More preferably, the compounds inhibiting the binding between TAK1 and TAB1 may be compounds that specifically bind to the binding site of TAK1 to TAB1, or the binding site of TAB1 to TAK1.

Such compounds inhibiting the binding between TAK1 and TAB1 include proteins, peptides, and chemically synthesized compounds, for example, TAK1 or TAB1 mutants, partial peptides of TAK1 or TAB1, antibodies against TAK1 or TAB1, compounds that specifically bind to TAK1, TAB1, or both, or antisense oligonucleotides of TAK1 or TAB1.

There is no particular limitation on the structure, origin, and such of the compound inhibiting the binding between TAK1 and TAB1, as far as the compound has the activity of inhibiting the binding between TAK1 and TAB1.

A specific example of the compound inhibiting the binding between TAK1 and TAB1 is TAK1-DN as described below in Examples. TAK1-DN has the amino acid sequence from amino acid 77 Glu to amino acid 303 Gln in the amino acid sequence of SEQ ID NO: 2. TAK1-DN has TAB1-binding activity but lacks in TAK1 kinase activity. Accordingly, TAK1-DN can bind to TAB1 but not induces the signal transduction through TAK1. As a consequence, TAK1-DN inhibits the binding between normal TAK1 and TAB1. Thus, TAK1-DN can be a specific example of the compound inhibiting the signal transduction through TAK1.

The compound inhibiting the binding between TAK1 and TAB1 can be obtained by using the screening system with TAK1 and TAB1. Such a system screening with TAK1 and TAB1 includes the screening system using ELISA or two-hybrid system as described herein.

The compound inhibiting the kinase activity of TAK1 may be a compound inhibiting TAK1 activation or a compound inhibiting the catalytic function of TAK1. The compound inhibiting TAK1 activation includes, for example, the above-mentioned compound inhibiting the binding between TAK1 and TAB1, or a compound inhibiting TAK1 activation accompanying the binding with TAB1.

These compounds may be compounds that specifically bind to the respective targets, compete for the targets with the proteins which bind to the targets, and the competitive binding keeps the proteins which bind to the targets free from the targets. These compounds may be compounds that specifically bind to the region where TAK1 and TAB1 bind to each other or to the TAK-1 activating region of the TAB1 and thereby inhibiting the binding between TAK1 and TAB1 or inhibiting TAK1 activation accompanying the binding.

The compounds inhibiting the kinase activity of TAK1 can also be compounds that act on the catalytic region of TAK1 and inhibit the phosphorylation ability of activated TAK1. For example, such compounds can be compounds that inhibit the catalytic action in the phosphorylation or the interaction with the substrate. These compounds may be compounds that specifically bind to the respective targets, compete for the targets with the proteins which bind to the targets, and the competitive binding keeps the proteins which bind to the targets free from the targets. These compounds may be compounds that specifically bind to the catalytic region of TAK1 or the region binding to substrate protein in TAK1, TAK1-binding region of a substrate protein, or the region to be phosphorylated by TAK1, and thereby inhibiting the binding between TAK1 and its substrate or inhibiting the phosphorylation by TAK1 accompanying the binding. Such a compound inhibiting TAK1 kinase activity can be obtained by using the in vitro kinase assay system as described above.

Such compounds inhibiting the signal transduction through TAK1 include proteins, peptides, and chemically synthesized compounds, for example, TAK1 or TAB1 mutants, partial peptides of TAK1 or TAB1, antibodies against TAK1 or TAB1, compounds that specifically bind TAK1, TAB1, or both, or antisense oligonucleotides of TAK1 or TAB1. There is no particular limitation on the structure, origin, and such of the compound inhibiting the signal transduction through TAK1, as far as the compound has the activity of inhibiting the signal transduction through TAK1. The compound inhibiting the signal transduction through TAK1 includes a compound of which structure is in part modified by addition, deletion, and/or substitution.

As described below in Examples, it has been revealed that the compound inhibiting the signal transduction through TAK1 inhibits the production of inflammatory cytokines such as IL-1, TNF, and IL-6 induced by an inflammatory stimulus (LPS) and also inhibits IL-6 production that is induced by an inflammatory cytokine (IL-1). Accordingly, the compound inhibiting the signal transduction through TAK1 is useful for inhibiting the signal transduction through these inflammatory cytokines, the production of inflammatory cytokines induced thereby, the physiological activity of inflammatory cytokines, the signal transduction through inflammatory stimulation, and/or inflammatory stimulation. It is known that cytokines such as IL-1, TNF, and IL-6 are involved in inflammatory reaction and therefore are collectively called inflammatory cytokine.

These inflammatory cytokines are assumed to be involved in the advancement of various diseases such as sepsis, rheumatoid arthritis, asthma, nephritis, hepatitis, and pneumonia. Thus, pharmaceutical compositions, which contain a compound inhibiting the signal transduction through TAK1, can be used for the treatment and/or prevention of these diseases.

Further, it is known that the inhibition of inflammatory stimulation-induced or cytokine network-associated production of inflammatory cytokines as well as the inhibition of physiological action of inflammatory cytokine reduces inflammation and suppresses the inflammatory action. Thus, the compound inhibiting the signal transduction through TAK1 has the anti-inflammatory effect suppressing the inflammatory stimulation and/or the physiological action of inflammatory cytokines. Accordingly, the compound inhibiting the signal transduction through TAK1 is useful as an anti-inflammatory agent. The compound inhibiting the signal transduction through TAK1 can be used for the expectation of the anti-inflammatory effect in treating diseases with inflammation.

The inventive inhibitor of the signal transduction through inflammatory cytokines, inhibitor of the production of inflammatory cytokines, anti-inflammatory agent, or pharmaceutical composition can be used in a usual manner when given as a pharmaceutical agent to human or other mammals, for example, mouse, rat, guinea pig, rabbit, chicken, cat, dog, sheep, pig, cow, monkey, hamadryas baboon, and chimpanzee.

For example, as required, the inventive inhibitor, agent, or composition can be used orally as a sugar coated tablet, capsule, elixir, or microcapsule, or used parenterally as an injection of sterile solution or suspension thereof in water or any other pharmaceutically acceptable liquid.

For example, the product can be manufactured by mixing the inventive inhibitor of the production of inflammatory cytokines or anti-inflammatory agent with a physiologically acceptable carrier, flavoring agent, filler, vehicle, preservative, stabilizer, and/or binder in generally acceptable unit dose formulation which is required for drug manufacture. In such a preparation, the amount of the active ingredient should be an appropriate dose within an indicated range of dose.

Additives that can be mixed to tablet and capsule include, for example, binders such as gelatin, corn starch, gum tragacanth, and gum Arabic, fillers such as crystalline cellulose, swelling agents such as corn starch, gelatin, and alginic acid, lubricants such as magnesium stearate, sweetener such as sucrose, lactose, and saccharin, and flavoring agents such as peppermint, Gaultheria adenothrix oil, and cherry.

When the dosage form is a capsule, it can contain a liquid carrier such as fatty oil in addition to the above-mentioned materials. The sterile composition for injection can be formulated with a vehicle such as distilled water for injection according to a commonly used procedure for drug manufacture.

Aqueous solutions for injection include, for example, physiological saline, isotonic solution containing glucose or other adjuvants, for example, D-sorbitol, D-mannose, D-mannitol, or sodium chloride, which can be used together with an appropriate solubilizer, for example, alcohol, specifically, ethanol, polyalcohol, for example, propylene glycol, polyethylene glycol, nonionic detergent, for example, polysorbate 80 or HCO-50.

The oil is exemplified by sesame oil and soybean oil, and it can be used together with benzyl benzoate or benzyl alcohol as a solubilizer. A buffer (e.g., phosphate buffer and sodium acetate buffer), pain-killer (e.g., procaine hydrochloride), stabilizer (e.g., benzyl alcohol and phenol), or antioxidant can be formulated into the preparation. The formulated solution for injection is generally filled into an appropriate ampul.

Dosage of the inventive inhibitor of the production of inflammatory cytokines or anti-inflammatory agent varies depending on symptoms but generally is about 0.1 to 100 mg a day, preferably about 1.0 to 50 mg a day, and more preferably about 1.0 to 20 mg a day, for human adult (in the case of body weight 60 kg) when given orally.

In the case of parenteral administration, its single dose can vary depending on the type of subject and organ to be given, symptoms, and administration procedures but it is preferable to typically administer, for example, about 0.01 to 30 mg a day, preferably about 0.1 to 20 mg a day, more preferably about 0.1 to 10 mg a day by intravenous injection for human adult (in the case of body weight 60 kg) when given as an injection. The drug can be given to other animals and the dose to be given can be converted based on the dosage for body weight of 60 kg.

BEST MODE FOR CARRYING OUT THE INVENTION

The present invention is illustrated in detail below with reference to Examples and a Reference Example, but is not to be construed as being limited thereto.

Example 1

Construction of TAK1-DN Expression Vector and Creation of Transgenic Mice

A TAK1-DN expression vector that acts as a dominant negative inhibitor was prepared to demonstrate that the signal transduction through LPS or inflammatory cytokines can be inhibited by inhibiting the specific binding between human TAK1 and human TAB1.

TAK1-DN has the amino acid sequence, corresponding to the TAB1-binding region of TAK1, which covers a stretch from amino acid 77 Glu to amino acid 303 Gln in the amino acid sequence of SEQ ID NO: 2. The TAK1-DN-encoding gene fragment was amplified by using ph-TAK1 (refer to Unexamined Published Japanese Patent Application (JP-A) No. Hei 9-163990) as a template DNA by PCR. Specifically, a sense primer TAK1S (SEQ ID NO: 5) containing a recognition site for restriction enzyme EcoRI and the initiation codon ATG and an antisense primer TAK1AS (SEQ ID NO: 6) containing a recognition site for restriction enzyme EcoRI and the stop codon were used to amplify the TAK1-DN-encoding DNA fragment.

Figure 1:
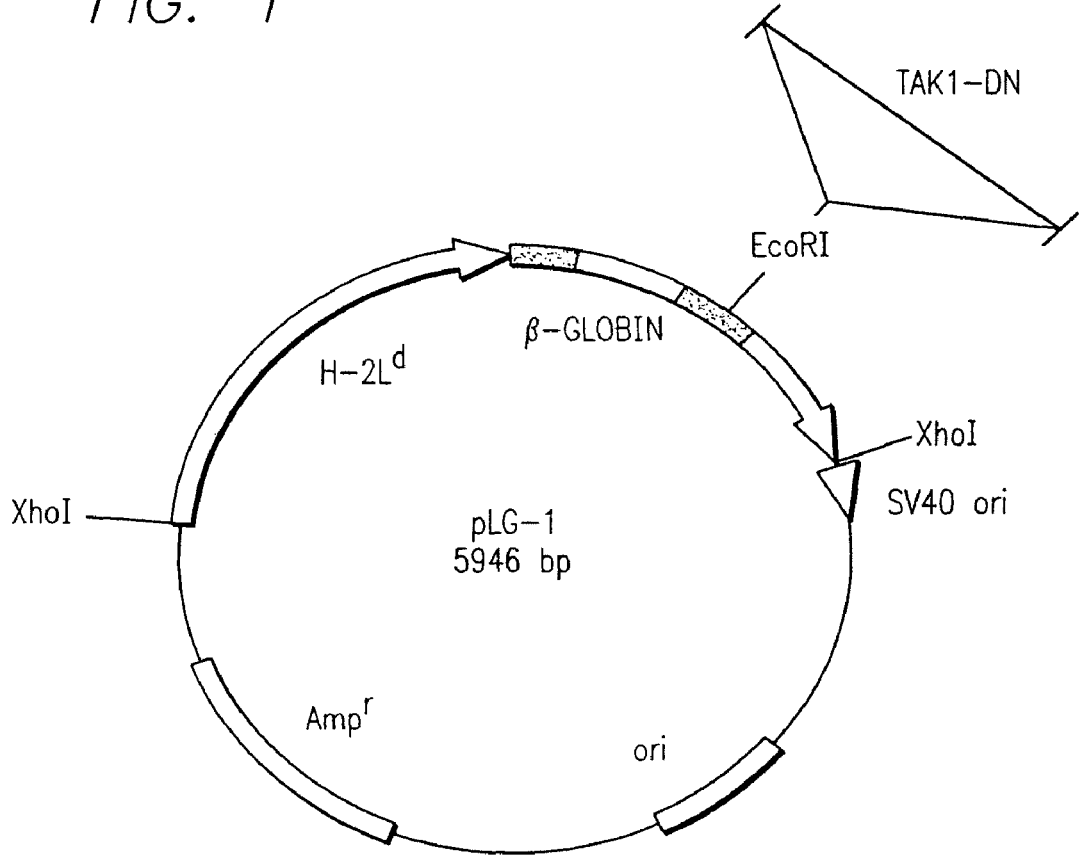
FIG. 1 shows a schematic illustration of the structure of TAK1-DN expression vector used in the preparation of transgenic mice.

The resulting PCR products were digested with restriction enzyme EcoRI and then inserted at an EcoRI site of animal cell expression vector pLG-1 (see FIG. 1) containing H-2L$^d$ promoter to prepare TAK1-DN transgenic vector pLG-TAKDN.

DNA was introduced by microinjection under an inverted microscope (LEICA) with Nomarski differential-interference device by using glass micropipettes connected with a micromanipulator. Specifically, 2 pl of solution of TAK1-DN-encoding DNA molecule (about 500 molecules of in 1-pl PBS) was injected into a male pronucleus in a fertilized egg from C57BL/6J mouse. The gene fragment for the introduction was prepared by digesting pLG-TAKDN with restriction enzyme XhoI and then separating and purifying it by agarose gel electrophoresis.

The manipulated egg with introduced DNA was transplanted in an oviduct of pseudopregnant female mouse (recipient mouse) of ICR strain. The pseudopregnancy was induced by mating with a male mouse that had undergone vasoligation. Nineteen days after the transplantation, the neonatal mice were born by normal spontaneous delivery or by Caesarean section. The neonatal mice born by Caesarean section were nursed by another female mouse of ICR strain that had been arranged previously as a foster mother.

DNAs were prepared from tails of the neonatal mice at the age of 3 to 4 weeks, to test the presence of the introduced sequence by PCR. The DNAs for the analysis were prepared as follows. Specifically, each 2-cm tail section was lysed in a 1-ml lysis buffer (20 mM Tris-HCl, pH 7.0, 100 mM NaCl, 20 mM EDTA, 1% SDS, 1 mg/ml Proteinase K) at 55° C. overnight. After a series of phenol extraction, phenol-chloroform extraction, and chloroform extraction, the DNA was extracted by isopropanol-precipitation. The DNA obtained was dissolved in 100 μl TE (10 mM Tris-HCl, pH 8.0, 1 mM EDTA).

PCR analysis was carried out by using the DNA (100 ng) as a template and PCR primers Rb-glol (SEQ ID NO: 7) and TA12A (SEQ ID NO: 8). The analysis revealed that, of the 22 mice, 3 males and 2 females had the new gene.

Figure 2:
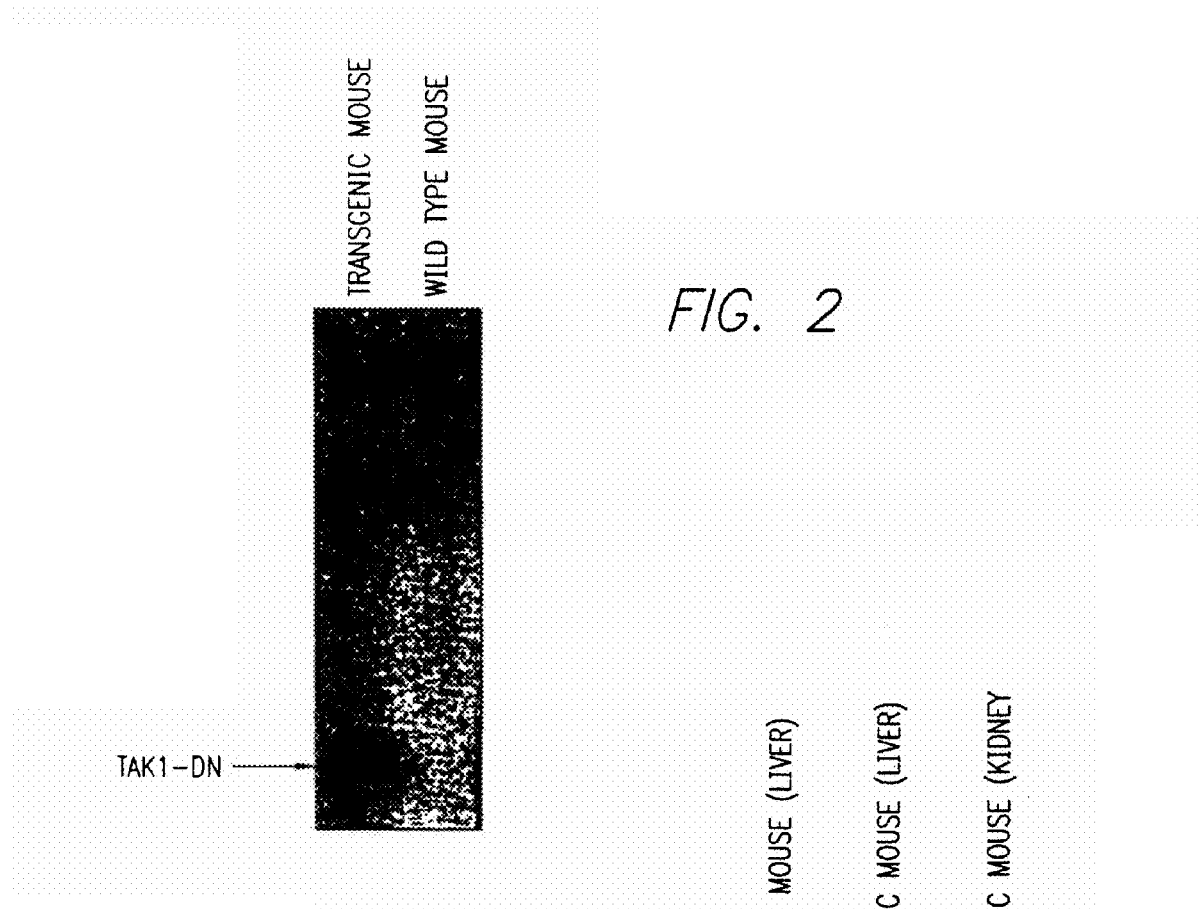
FIG. 2 shows a result of Southern analysis of DNA for TAK1-DN expression vector, which is integrated into transgenic mouse founders.

FIG. 2 shows a result of genomic Southern analysis. Specifically, EcoRI-digested genomic DNA (50 μg) was electrophoresed on a 0.7% agarose gel, and transferred onto a nylon membrane Hybond N+ (Amersham). The membrane was hybridized to a probe of TAK1-DN DNA (50 ng) labeled with [$\alpha$-$^{32}$P] dCTP according to a usual method. The result showed that bands of interest were detected in only TAK1-DN transgenic mice, and the presence of introduced gene was confirmed.

A line (female) of the above-mentioned created mice was mated with a C57BL/6J male mouse for the first generation. The obtained mice were analyzed for the presence or absence of the introduced gene in the same manner as described above. The result showed that the introduced gene was inherited in 11 of the 25 $F_1$ mice.

Figure 3:
FIG. 3 shows a result of Northern analysis of mRNAs from F1 generation of transgenic mouse in which TAK1-DN expression vector is integrated.

FIG. 3 shows a result of verification of actual mRNA expression of TAK1-DN in $F_1$ mice. Specifically, total RNAs were prepared from the livers and kidneys of $F_1$ mice, and 30-μg aliquots of them were electrophoresed on a denaturation agarose gel with 1% formalin. The RNAs were transferred onto a nylon membrane Hybond N+ (Amersham) and hybridized to a probe of TAK1-DN DNA (50 ng) labeled with [$\alpha$-$^{32}$P] dCTP according to a usual method. The result showed that bands of interest were detected in only $F_1$ mice, and the expression of introduced gene was confirmed.

The transgenic mouse lines were subcultured and maintained by using external fertilization. Specifically, 48 hours after the injection of 5 IU pregnant mare serum gonadotropin (PMSG, TEIKOKU HORMONE Mfg. Co.), a dose of the same units of human chorionic gonadotropin (hCG, Sankyo) was injected in a C57BL6/J female mouse, followed by mating with a $F_1$ male mouse. Then, 16 to 17 hours after the injection of hCG, sperms were collected from the caudal portion of a male mouse. The sperms were incubated in a TYH medium (the 1-ml medium contains NaCl 6.97 mg, KCl 0.36 mg, $CaCl_2.2H_2O$ 0.25 mg, $KH_2PO_4$ 0.16 mg, $MgSO_4.7H_2O$ 0.29 mg, $NaHCO_3$ 2.11 mg, sodium pyruvate 0.11 mg, streptomycin 50 μg, penicillin 75 μg, and glucose 1.0 mg, pH 7.0) containing 4 mg/ml BSA at 37° C. for 1.5 hours. Immediately before the end of the incubation, eggs were collected from a C57BL6/J female mouse and placed in a TYH medium containing 4 mg/ml BSA under oil. Then the sperms were added to the medium containing the eggs, and the mixture was incubated at 37° C. for 4 to 6 hours. The resulting fertilized eggs were transferred in a Whitten's medium (the 1-ml medium contains NaCl 5.14 mg, KCl 0.36 mg, $KH_2PO_4$ 0.16 mg, $MgSO_4.7H_2O$ 0.29 mg, $NaHCO_3$ 1.90 mg, calcium lactate pentahydrate 0.53 mg, streptomycin 50 μg, penicillin 80 μg, glucose 1.0 mg, and 3.7 mg of 60% sodium lactate) containing 100 mM EDTA and 4 mg/ml BSA, and transplanted in the oviduct of a female mouse after removing the sperms.

Example 2

Cytokine Production Capacity of Peritoneal Macrophages Expressing TAK1-DN

Peritoneal macrophages were prepared from TAK1-DN-expressing transgenic mice, and the responses of the cells to IL-1 and lipopolysaccharide (LPS; Sigma) were examined.

Specifically, 10 ml of ice-cold PBS solution containing 0.36% sodium citrate was injected into the peritoneal cavity of a TAK1-DN-expressing transgenic mouse (TAK1-DN Tgm) or a C57BL/6 mouse (wild-type mouse) of the same weeks of age. The mouse was given a massage for 30 seconds, and then the solution was recovered from the mouse. The solution recovered was centrifuged, and the precipitated cells were resuspended in RPMI1640 (GIBCO-BRL) containing 10% FBS (GIBCO-BRL). The cells were plated in wells at a cell density of $5\times10^4$/well. The cells were cultured at 37° C. for 2 hours, and floating cells were removed by washing with media. Cells adsorbed on the culture plate were used as peritoneal macrophages.

LPS, at a final concentration of 10 μg/ml, or IL-1α (Genzyme), at a final concentration of 10 ng/ml, was added to the above-prepared peritoneal macrophages, and the cells were further cultured for 24 hours. The culture supernatant was recovered. Then, the amounts of IL-1β in the culture supernatant of LPS-stimulated macrophages and IL-6 in the culture supernatant of IL-1α-stimulated macrophages were assayed by ELISA kits (Genzyme).

Figure 4:
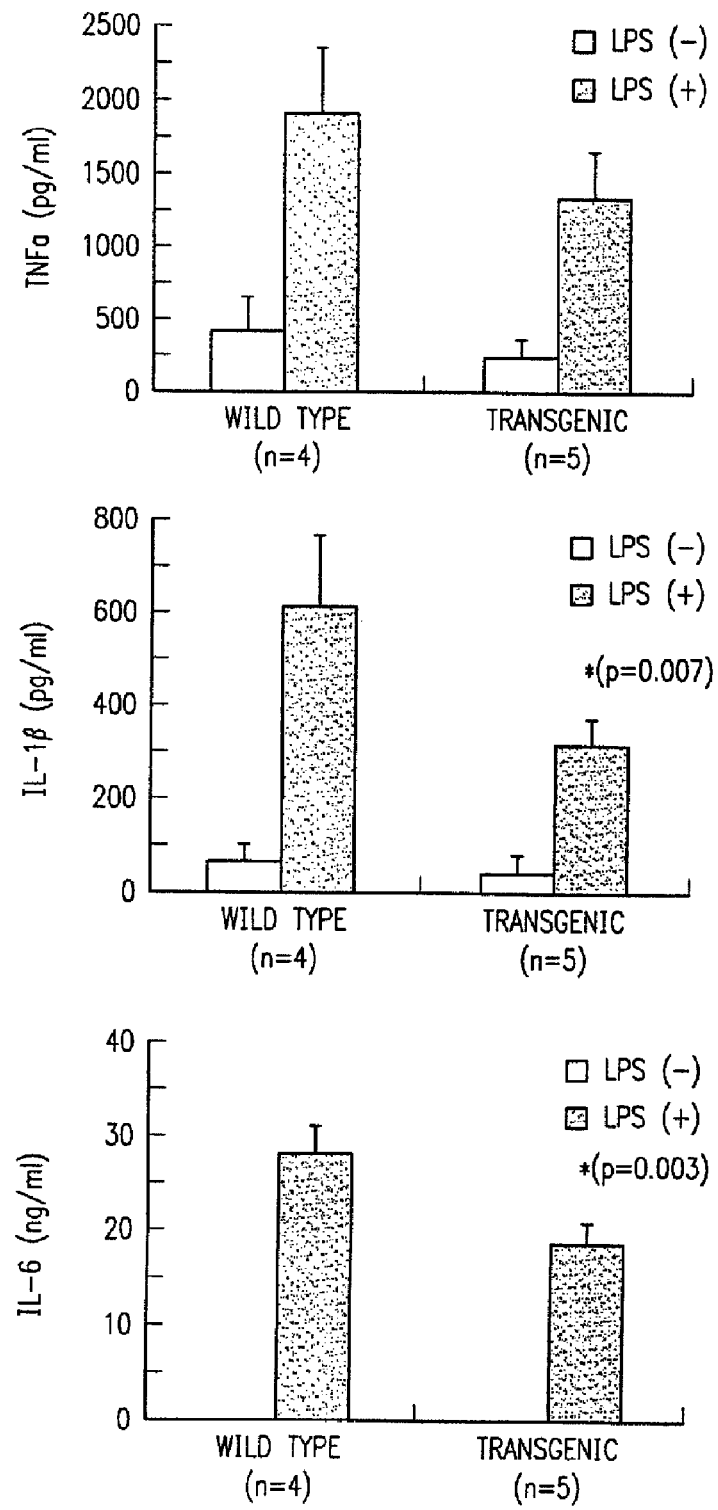
FIG. 4 shows an analytical result for the induction of production of TNF, IL-1, and IL-6 in LPS-stimulated peritoneal macrophages derived from TAK1-DN-expressing transgenic mouse.
Figure 5:
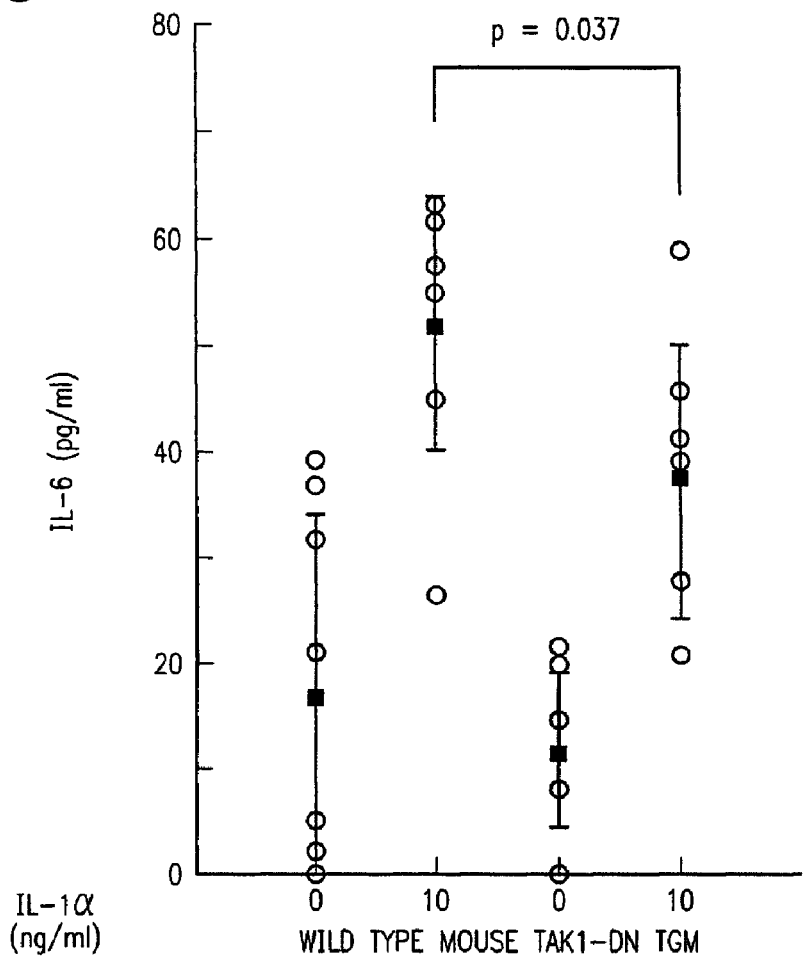
FIG. 5 shows an analytical result for the induction of IL-6 production in IL-1α-stimulated peritoneal macrophages derived from TAK1-DN-expressing transgenic mouse. Observed values (open circle) in multiple sets of experiment and the means (closed square) ±S.D. are displayed.

The results are shown in FIGS. 4 and 5. LPS-stimulated induction of production of TNF, IL-1β, and IL-6 is evaluated in FIG. 4. The induction of production of these inflammatory cytokines was significantly inhibited in TAK1-DN Tgm-derived macrophages as compared with wild-type mouse-derived macrophages. Likewise, the induction of IL-6 production was significantly inhibited in TAK1-DN Tgm-derived macrophages as compared with wild-type mouse-derived macrophages, as seen in FIG. 5 showing the result of experiment for the induction of IL-6 production by IL-1 stimulation. The described results indicate that inhibition of the binding between TAK1 and TAB1 suppresses the inflammatory stimulation (LPS)-induced production of inflammatory cytokines as well as suppresses the cytokine production based on the inflammatory cytokine network.

Example 3

IκBα Degradation in TAK1-DN Expressing Peritoneal Macrophages Stimulated by LPS and IL-1α

The macrophages derived from wild-type mice and from TAK1-DN Tgm, which were prepared as described above, were stimulated by LPS or IL-1, and the time course of degradation of IκBα by proteasome was monitored (0, 30, and 60 minutes). Specifically, the peritoneal macrophages were cultured in wells of a 96-well plate at a cell density of $1\times10^6$/well. LPS (1 μg/ml) or IL-1α (10 ng/ml) was added to the culture in the presence or absence of proteasome inhibitor MG132 (40 μM). The cells were harvested after 30 or 60 minutes.

Figure 6:
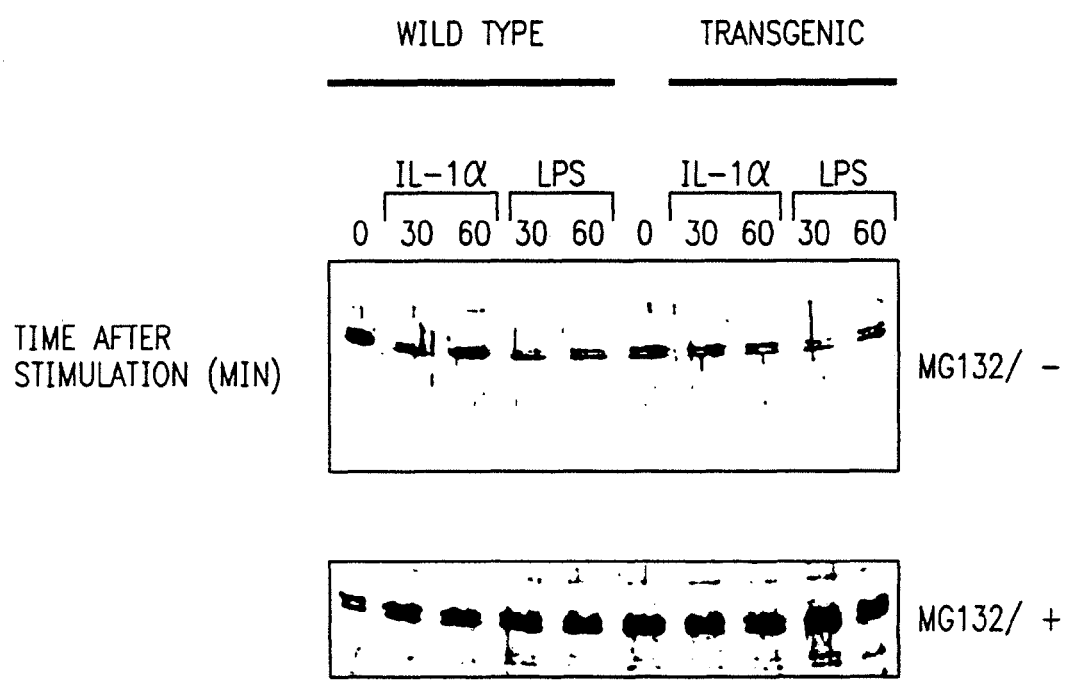
FIG. 6 shows an analytical result for the degradation of IκBα by proteasome in LPS-stimulated and IL-1α-stimulated peritoneal macrophages derived from TAK1-DN-expressing transgenic mouse.

The cells were washed with PBS (−), and then a lysis buffer was added thereto for the preparation of cell lysate. An aliquot of each lysate corresponding to about 2×10$^5$ cells was subjected to gel electrophoresis by 9% SDS-PAGE. The fractionated proteins were blotted onto a nitrocellulose membrane and then incubated with anti-IκBα antibody (SantaCruz) as a primary antibody for 1.5 hours. After wash, horseradish peroxidase-conjugated goat anti-rabbit antibody was used as a secondary antibody. After the reaction of the secondary antibody, the reaction product was detected by using ECL (Amersham). As seen in FIG. 6, rapid degradation of IκBα was observed in a control experiment with wild-type mouse-derived macrophages stimulated by LPS and IL-1, suggesting the induction of NFκB activation. On the other hand, no remarkable degradation of IκBα was observed in TAK1-DN Tgm-derived macrophages even when the cells were stimulated by LPS and IL-1, suggesting the suppression of NFκB activation. Thus the present Example revealed at the molecular biological level that the inhibition of signal transduction through TAK1 can significantly inhibit the activation of NFκB.

Reference Example 1

The animal cell two-hybrid system (Dang et al., (1991) Mol. Cell. Biol. 11, 954-962) using TAB1 peptide and TAK1 peptide was used to analyze whether or not a peptide (TAK1-DN) from Glu at amino acid 77 to Gln at amino acid 303 in the TAK1 peptide of SEQ ID NO: 2 is capable of inhibiting the binding between TAK1 peptide and TAB1 peptide and further capable of inhibiting TAK1 peptide activation in animal cells.

First, each of genes encoding full-length TAK1 and TAK1-DN was ligated with the gene encoding GAL4 DNA-binding domain (GAL4-BD) to prepare an expression vector. The gene encoding full-length TAK1 was obtained from yeast two-hybrid expression plasmid pBTMHu11F (Shibuya H. et al., (1996) 272, 1179-1182) by digesting it with restriction enzymes EcoRI and PstI. Subsequently, the gene was ligated between EcoRI and PstI sites of an expression vector pM (CLONTECH) containing the GAL4-BD gene to obtain an animal cell two-hybrid expression plasmid pM-TAK1.

In the next step, the gene encoding TAK1-DN was amplified by PCR using a sense primer DNTAK5' (SEQ ID NO: 9) with a recognition site for restriction enzyme EcoRI and an antisense primer DNTAK3' (SEQ ID NO: 10) with a site for restriction enzyme PstI by using plasmid pBTMHu11F as a template DNA. The amplified DNA was digested with restriction enzymes EcoRI and PstI, and then ligated into pM vector, thereby constructing animal cell two-hybrid expression plasmid pM-TAK1DN.

Subsequently, the gene encoding TAB1C68 consisting of C-terminal 68 amino acid residues of TAB1 peptide was ligated with the gene encoding transcription activation domain (VP16-AD) from VP16 protein of herpes simplex virus to prepare an expression vector. The gene encoding TAB1C68 was prepared by digesting yeast two-hybrid expression plasmid pGAD-TAB1 (Shibuya H. et al., (1996) 272, 1179-1182) by restriction enzyme EcoRI, and then the gene was ligated at an EcoRI site of expression vector pVP16 (CLONTECH) containing the gene encoding VP16-AD, and thereby obtaining animal cell two-hybrid expression plasmid pVP16-C68.

The reporter plasmid used was pG5-Luc, which was constructed from pG5CAT (CLONTECH) containing 5 consecutive GAL4-binding sites and the chloramphenicol acetyltransferase (CAT) gene downstream thereof. pG5-Luc contains the luciferase gene substituted instead of the CAT-encoding gene in the pG5CAT.

After cultured overnight, CHO cells (5×10$^4$ cells/each well) were washed with PBS. A mixture of 500 ng of GAL4-BD fusion protein expression plasmid (any one of pM, pM-TAK1, and pM-TAK1DN), 500 ng of VP16-AD fusion protein expression plasmid (pVP16 or pVP16-C68), 100 ng of reporter plasmid pG5-Luc, 50 ng of pRL-SV40 (containing the *Renilla luciferase* gene downstream of SV40 promoter; Promega) and 10 μl LIPOFECTAMINE (GIBCO-BRL) was added to the cell culture, and the culture was continued for 5 hours to achieve the introduction of the genes.

Figure 7:
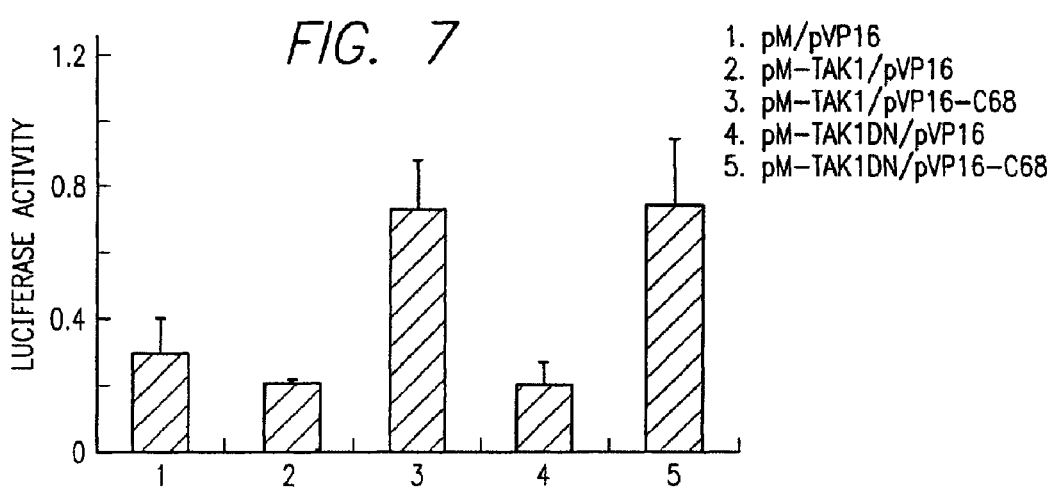
FIG. 7 shows a graph indicating a result of two-hybrid assay using CHO cells. The result shows means ±S.D. for the luciferase activity in cell extracts prepared from 3 wells.

The culture further continued for 72 hours, and then luciferase activities in each cell extract were assayed by using Dual-Luciferase™ Reporter Assay System (Promega). Specifically, the cells were washed with PBS, 250 μl of Passive Lysis Buffer attached to the kit was added thereto, and the mixture was incubated at room temperature for 15 minutes. A 20-μl aliquot of each cell extract was used for the assay. The efficiency of gene introduction was normalized by using measured values for the activity of *Renilla luciferase* derived from the introduced pRL-SV40. The result is shown in FIG. 7.

The elevation of luciferase activity was found in the combination of pM-TAK1DN and pVP16-C68 as well as the combination of pM-TAK1 and pVP16-C68. This shows that, like full-length TAK1, TAK1-DN is also capable of binding to TAB1.

INDUSTRIAL APPLICABILITY

The present invention has revealed that TAK1 participates in the signal transduction through inflammatory cytokines such as IL-1, TNF, or IL-6, and that compounds inhibiting the TAK1-associated signal transduction inhibit the production of inflammatory cytokines such as IL-1, TNF, and IL-6. Accordingly, the inventive screening method is useful to screen compounds inhibiting the production of inflammatory cytokines. Further, the inventive compounds inhibiting the TAK1-associated signal transduction are useful as inhibitors of the signal transduction through inflammatory cytokines, inhibitors of the production of inflammatory cytokines, inhibitors of the physiological activities of inflammatory cytokines, and inhibitors of the signal transduction through inflammatory stimulation. Further, compounds inhibiting the signal transduction through TAK1 are useful as anti-inflammatory agents.

The invention claimed is:

1. A method of screening for compounds that inhibit production of IL-6 produced in response to TNF, comprising:
   (a) providing a sample comprising a TGF-β-activated kinase 1 (TAK1) and a TAK1 binding protein 1 (TAB1);
   (b) contacting a test compound with the sample;
   (c) detecting binding between the TAK1 and the TAB1;
   (d) selecting a compound that inhibits the binding;
   (e) providing a cell expressing TAK1 and TAB1;
   (f) contacting the cell with TNF and the selected compound; and
   (g) determining whether the selected compound inhibits production of IL-6 in response to TNF;

wherein the TAK1 of (a) is selected from the group consisting of
   (i) a protein comprising amino acids 76 to 303 of SEQ ID NO:2; and
   (ii) a protein that binds to amino acids 437 to 504 of SEQ ID NO:4 and comprises an amino acid sequence encoded by a DNA sequence that hybridizes with the complement of nucleotides 408 to 1091 of SEQ ID NO:1 under washing conditions of 42° C., 5 ×SSC, 0.1% sodium dodecyl sulfate, and 50% formamide;

and wherein the TAB1 of (a) is selected from the group consisting of (iii) a protein comprising amino acids 437 to 504 of SEQ ID NO:4; and (iv) a protein that binds to amino acids 76 to 303 of SEQ ID NO:2 and comprises an amino acid sequence encoded by a DNA that hybridizes with the complement of nucleotides 1338 to 1541 of SEQ ID NO:3 under washing conditions of 42° C., 5 ×SSC, 0.1% sodium dodecyl sulfate, and 50% formamide.

2. The method of claim 1, wherein the TAK1 and/or the TAB1 is fused with a peptide.

3. The method of claim 1, wherein the TAK1 or the TAB1 is linked to a support.

4. The method of claim 1, wherein a label is attached to the TAK1 or the TAB1 and the binding is detected by detecting or measuring the label.

5. The method of claim 1, wherein the binding is detected by detecting or measuring the TAB1 bound to the TAK1 with a primary antibody against TAB1 or a primary antibody against a peptide fused with the TAB1.

6. The method of claim 1, wherein the binding is detected by detecting or measuring the TAK1 bound to the TAB1 with a primary antibody against TAK1 or a primary antibody against a peptide fused with the TAK1.

7. The method of claim 1, wherein the binding is detected by detecting or measuring the TAB1 bound to the TAK1 with a primary antibody against the TAB1 or a primary antibody against a peptide fused with TAB1, and a secondary antibody against the primary antibody.

8. The method of claim 1, wherein the binding is detected by detecting or measuring the TAK1 bound to the TAB1 with a primary antibody against TAK1 or a primary antibody against a peptide fused with the TAK1, and a secondary antibody against the primary antibody.

9. The method of claim 8, wherein the primary antibody or the secondary antibody is labeled with a radioisotope, enzyme, or fluorescent substance.

10. The method of claim 1, wherein the TAK1 of (a) comprises amino acids 76 to 303 of SEQ ID NO:2.

11. The method of claim 1, wherein the TAK1 of (a) is a protein that binds to amino acids 437 to 504 of SEQ ID NO:4 and comprises an amino acid sequence encoded by a DNA that hybridizes with the complement of nucleotides 408 to 1091 of SEQ ID NO:1 under washing conditions of 42° C., 5 ×SSC, 0.1% sodium dodecyl sulfate, and 50% formamide.

12. The method of claim 1, wherein the TAK1 of (a) is a protein that binds to amino acids 437 to 504 of SEQ ID NO:4 and comprises an amino acid sequence encoded by a DNA that hybridizes with the complement of nucleotides 408 to 1091 of SEQ ID NO:1 under washing conditions of 60° C., 0.1 ×SSC, and 0.1% sodium dodecyl sulfate.

13. The method of claim 1, wherein the TAB1 of (a) comprises amino acids 437 to 504 of SEQ ID NO:4.

14. The method of claim 1, wherein the TAB1 of (a) is a protein that binds to amino acids 76-303 of SEQ ID NO:2 and comprises an amino acid sequence encoded by a DNA that hybridizes with the complement of nucleotides 1338 to 1541 of SEQ ID NO:3 under washing conditions of 42° C., 5 ×SSC, 0.1% sodium dodecyl sulfate, and 50% formamide.

15. The method of claim 1, wherein the TAB1 of (a) is a protein that binds to amino acids 76-303 of SEQ ID NO:2 and comprises an amino acid sequence encoded by a DNA that hybridizes with the complement of nucleotides 1338 to 1541 of SEQ ID NO:3 under washing conditions of 60° C., 0.1 ×SSC, and 0.1% sodium dodecyl sulfate.

16. The method of claim 1, wherein the selected compound inhibits production of IL-6 produced in response to TNF.

\* \* \* \* \*